US008771983B2

(12) United States Patent
Shimizu

(10) Patent No.: US 8,771,983 B2
(45) Date of Patent: Jul. 8, 2014

(54) METHOD AND KIT FOR EXPRESSING PROTEIN UNDER REGULATION OF THE EXPRESSION FROM REPEATED SEQUENCE FORMED BY GENE AMPLIFICATION, AND TRANSFORMANT

(75) Inventor: Noriaki Shimizu, Hiroshima (JP)

(73) Assignee: National University of Corporation Hiroshima University, Hiroshima (JP)

(*) Notice: Subject to any disclaimer, the term of this patent is extended or adjusted under 35 U.S.C. 154(b) by 1244 days.

(21) Appl. No.: 11/889,512

(22) Filed: Aug. 14, 2007

(65) Prior Publication Data

US 2008/0032341 A1 Feb. 7, 2008

Related U.S. Application Data

(63) Continuation of application No. 11/667,963, filed as application No. PCT/JP2005/020972 on Nov. 15, 2005.

(30) Foreign Application Priority Data

| Nov. 18, 2004 | (JP) | ................................. | 2004-334984 |
| Apr. 19, 2005 | (JP) | ................................. | 2005-121431 |

(51) Int. Cl.
    *C12N 15/85*     (2006.01)
    *C12N 15/87*     (2006.01)
    *C12N 15/90*     (2006.01)
    *C12N 15/113*     (2010.01)
    *C12N 5/16*     (2006.01)

(52) U.S. Cl.
    USPC ......... 435/69.1; 435/70.3; 435/358; 435/455; 435/465

(58) Field of Classification Search
    None
    See application file for complete search history.

(56) References Cited

U.S. PATENT DOCUMENTS 4,634,665 A * 1/1987 Axel et al. ................... 435/69.1

5,994,132 A      11/1999 Chamberlain et al.
(Continued)

FOREIGN PATENT DOCUMENTS

| JP | 2003-245083 | 9/2003 |
| JP | 2004-135532 | 5/2004 |
| JP | 2004-337066 | 12/2004 |

OTHER PUBLICATIONS

Meneguzzi et al., 1984, "Plasmidial Maintenance in Rodent Fibroblasts of a BPV1-pBR322 Shuttle Vector Without Immediately Apparent Oncogenic Transformation of the Recipient Cells," EMBO Journal, vol. 3, No. 2, pp. 365-371.*

(Continued)

*Primary Examiner* — Manjunath Rao
*Assistant Examiner* — William W Moore
(74) *Attorney, Agent, or Firm* — Harness, Dickey & Pierce, P.L.C.

(57) ABSTRACT

A method is disclosed for releasing the transcriptional regulation caused by a repeated sequence in a gene, a kit therefor and so on to thereby establish a system capable of producing a protein in a large amount. At least one embodiment of the method can be achieved by any one or more of the following methods: (a) in the amplification of a gene encoding a target protein, co-amplifying a polynucleotide of 10 kbp or more such as a λ-phage DNA or an insulator sequence; (b) selecting by culturing cells having undergone gene amplification in media containing a drug with a gradual increase in concentration; (c) elevating the promoter activity of inducing the expression of a gene encoding a target protein; (d) excising an amplified gene region from a chromosome with the use of Cre-LoxP System; (e) treating cells having undergone gene amplification with 5-aza-2'-deoxycytidine to thereby lower the methylation degree of DNA; and (f) selecting the mammalian cells having undergone gene amplification on double minute chromosomes.

9 Claims, 23 Drawing Sheets

(56) References Cited

U.S. PATENT DOCUMENTS

| | | | |
|---|---|---|---|
| 6,027,722 A | 2/2000 | Hodgson | |
| 6,057,158 A | 5/2000 | Chamberlain et al. | |
| 6,063,622 A | 5/2000 | Chamberlain et al. | |
| 6,083,750 A | 7/2000 | Chamberlain et al. | |
| 6,087,129 A * | 7/2000 | Newgard et al. | 435/69.4 |
| 6,110,707 A * | 8/2000 | Newgard et al. | 435/69.4 |
| 6,133,503 A | 10/2000 | Scheffler | |
| 6,251,640 B1 * | 6/2001 | Yao | 424/93.2 |
| 6,328,958 B1 | 12/2001 | Amalfitano et al. | |
| 6,410,722 B1 | 6/2002 | Price et al. | |
| 6,451,596 B1 | 9/2002 | Chamberlain et al. | |
| 6,479,279 B2 | 11/2002 | Ustav | |
| 6,599,744 B1 | 7/2003 | Askari | |
| 6,670,188 B1 | 12/2003 | Vogels et al. | |
| 6,797,265 B2 | 9/2004 | Amalfitano et al. | |
| 6,878,549 B1 | 4/2005 | Vogels et al. | |
| 6,890,736 B1 * | 5/2005 | Reddy et al. | 435/69.1 |
| 6,946,259 B2 * | 9/2005 | Wahl et al. | 435/7.8 |
| 7,037,716 B2 | 5/2006 | Vogels et al. | |
| 7,192,741 B2 * | 3/2007 | Otte et al. | 435/70.3 |
| 7,244,617 B2 * | 7/2007 | Fang et al. | 435/456 |
| 7,326,567 B2 * | 2/2008 | Saha | 435/320.1 |
| 7,666,405 B2 | 2/2010 | Amalfitano et al. | |
| 2002/0002272 A1 * | 1/2002 | Houghton et al. | 530/388.3 |
| 2003/0092083 A1 * | 5/2003 | Jeoung et al. | 435/7.23 |
| 2003/0108914 A1 * | 6/2003 | Hadlaczky | 435/6 |
| 2003/0232781 A1 | 12/2003 | Wolffe et al. | |
| 2004/0203158 A1 * | 10/2004 | Hackett et al. | 435/473 |
| 2006/0051324 A1 * | 3/2006 | Kirkin et al. | 424/93.7 |
| 2006/0172382 A1 * | 8/2006 | Otte et al. | 435/69.1 |
| 2007/0178585 A1 * | 8/2007 | Harrington et al. | 435/320.1 |
| 2007/0298458 A1 * | 12/2007 | Shimizu | 435/69.1 |
| 2009/0111144 A1 * | 4/2009 | Bebbington | 435/69.6 |

OTHER PUBLICATIONS

Okayama et al., 1985, "Bacteriophage Lambda Vector for Transducing a cDNA Clone Library into Mammalian Cells," Molecular and Cell Biology, vol. 5, No. 5, pp. 1136-1142.*
European Office Action for corresponding application 05806841.2.
European Office Action for corresponding application 07014897.8.
Carvell T. Nguyen et al. "Histone H3-Lysine 9 Methylation is Associated with Aberrant Gene Silencing in Cancel Cells and is Rapidly Reversed by 5-Aza-2'-deoxycytidine." Cancer Research, vol. 62, No. 22, Nov. 15, 2002, pp. 6456-6461.
Vesco Mutskov et al. "Silencing of transgene transcription precedes methylation of promoter DNA and histone H3 lysine 9." EMBO (European Molecular Biology Organization) Journal, vol. 23, No. 1, Jan. 14, 2004, pp. 138-149.
Jong-Mook Kim et al. "Improved recombinant gene expressions in CHO cells using matrix attachment regions." Journal of Biotechnology, vol. 107, No. 2, Jan. 22, 2004, pp. 95-105.
Mark C. Walters et al. "Transcriptional Enhancers Act in CIS to suppress position-effect variegation." Genes and Development, Cold Spring Harbor, NY, US, vol. 10, No. 2, Jan. 15, 1996, pp. 185-195.
Nathan B. Sutter et al. "Chromatin insulation by a transcriptional activator." Proceedings of the National Academy of Sciences of the United States of America. vol. 100, No. 3, Feb. 4, 2003, pp. 1105-1110.
J. Johansen et al. "Evaluation of Tet-on system to avoid transgene down-regulation in ex vivo gene transfer to the CNS." Gene Therapy, vol. 9, No. 19, Oct. 19, 2002, pp. 1291-1301.
Wang D. et al. "p125 focal adhesion kinase promotes malignant astrocytoma cell proliferation in vivo". Journal of Cell Science vol. 113, pp. 4221-4230. 2000. (in parent).
Sauer B et al. "Cre-stimulated recombination at loxP-containing DNA sequences placed into the mammalian genome." Nucleic Acids Research, vol. 17, pp. 147-161. 1989. (in parent).
Knobbe C. B. et al. "Hypermethylation and transcriptional downregulation of the carboxyl-terminal modulator protein gene in glioblastomas". Journal of the National Cancer institute, vol. 96, No. 6, pp. 483-486. 2004. (in parent).
Kang S. H. et al. "Transcriptional repression of the transforming growth factor-betta type I receptor gene by DNA methlation results in the development of TGF-beta resistance in human gastric cancer". Oncogene, vol. 18, No. 51, pp. 7280-7286. 1999. (in parent).
Naoyuki Hanada et al., "Establishment of a protein-overproducing system by using a novel and efficient gene amplification method," Abstracts of the subjects covered by the lectures on the 27th Annual Meeting of the Molecular Biology Society of Japan, 2004, p. 524 1PB-042, and English translation thereof.
Noriaki Shimizu et al., "Plasmids with a Mammalian Replication Origin and a Matrix Attachment Region Initiate the Event Similar to Gene Amplification." Cancer Research, vol. 61, p. 6987-6990, 2001.
Noriaki Shimizu et al., "Amplification of Plasmids Containing a Mammalian Replication Initiation Region Is Mediated by Controllable Conflict between Replication and Transcription." Cancer Research, vol. 63, p. 5281-5290, 2003.
Michael W. McBurney et al., "Evidence for Repeat-Induced Gene Silencing in Cultured Mammalian Cells: Inactivation of Tandem Repeats of Transfected Genes." Experimental Cell Research, vol. 274, p. 1-8, 2002.
Charlene McWhinney et al., "Autonomous replication of a DNA fragment containing the chromosomal replication origin of the human c-myc gene." Nucleic Acids Research, vol. 18, No. 5, p. 1233-1242, 1990.
Peter A. Dukwel et al., "Matrix Attachment Regions Are Positioned Near Replication Initiation Sites, Genes, and an Interamplicon Junction in the Amplified Dihydrofolate Reductase Domain of Chinese Hamster Ovary Cells." Molecular and Cellular Biology, vol. 8, No. 12, p. 5398-5409, 1988.
Mirit I. Aladjem et al. "Genetic Dissection of a Mammalian Replicator in the Human β-Globin Locus." Science, vol. 281, p. 1005-1009, 1998.
Ken Tsutsui et al., "Identification and Characterization of a Nuclear Scaffold Protein That Binds the Matrix Attachment Region DNA." The Journal of Biological Chemistry, vol. 268, p. 12886-12894, 1993.
Yves Pommier et al., "Identification within the Simian Virus 40 Genome of a Chromosomal Loop Attachment Site That Contains Topoisomerase II Cleavage Sites." Journal of Virology, vol. 64, No. 1, p. 419-423, 1990.
Laurie A. Quinn et al., "Cell Lines from Human Colon Carcinoma with Unusual Cell Products, Double Minutes, and Homogeneously Staining Regions." Cancer Research, vol. 39, p. 4914-4924, 1979.
Noriaki Shimizu et al., "Selective capture of acentric fragments by micronuclei provides a rapid method for purifying extrachromosomally amplified DNA." Nature Genetics, vol. 12, p. 65-71, 1996.
Félix Recillas-Targa et al., "Position-effect protection and enhancer blocking by the chicken β-globin insulator are separable activities." Proceeding of the National Academy of Science of the United States of America, vol. 99, No. 10, p. 6883-6888, 2002.
Koji Akasaka et al., "Upstream Element of the Sea Urchin Arylsulfatase Gene Serves as an Insulator." Cellular and Molecular Biology, vol. 45(5), p. 555-565, 1999.
J. Sambrook et al., "Molecular Cloning—A laboratory manual 3rd Ed." Cold Spring Harbor Laboratory Press, p. 4.82-4.85, 2001.
Susan M. Janicki et al., "From Silencing to Gene Expression: Real-Time Analysis in Single Cells." Cell, vol. 116, p. 683-698, 2004.
Gang Li et al., "Interphase Cell Cycle Dynamics of a Late-Replicating, Heterochromatic Homogeneously Staining Region: Precise Choreography of Condensation/Decondensation and Nuclear Positioning." The Journal of Cell Biology, vol. 140, No. 5, p. 975-989, 1998.
Teru Kanda et al., "The Dynamics of Acentric Chromosomes in Cancer Cells Revealed by GFP-Based Chromosome Labeling Strategies." Journal of Cellular Biochemistry Supplement 35, p. 107-114, 2000.
Steven E. Benner et al., "Double minute chromosomes and homogeneously staining regions in tumors taken directly from patients versus in human tumor cell lines." Anti-Cancer Drugs, 2, p. 11-25, 1991.

(56) References Cited

OTHER PUBLICATIONS

Noriaki Shimizu et al., "When, where and how the bridge breaks: anaphase bridge breakage plays a crucial role in gene amplification and HSR generation." Experimental Cell Research, 302, p. 233-243, 2005.

D.R. Shimishek et al., "Codon-Improved Cre Recombinase (iCre) Expression in the Mouse." genesis 32, p. 19-26, 2002.

Naoyuki Hanada et al., "Study for the establishment of the protein over-expression system using an efficient and novel gene amplification method in mammalian cells." Abstracts of the subjects covered by the lectures on the 28th Annual Meeting of the Molecular Biology Society of Japan, 1P-0621, and partial English language translation thereof. Nov. 2004.

Korean Notice of Patent Grant dated Mar. 26, 2010 for corresponding Korean Application No. 10-2007-7018478 (with English translation).

U.S. Office Action dated Apr. 13, 2010 for corresponding U.S. Appl. No. 11/667,963.

BD™ Tet-off and Tet-on Gene Expression Systems User Manual, BD Biosciences Clontech, Protocol PT3001-1, Ver. PR33678 (Mar. 14, 2003), (Momparler et al.).

DNA Methylation and Cancer, Journal of Cellular Physiology, vol. 183, pp. 145-154 (2000).

Naoyuki Hanada et al., "Study for the establishment of the protein over-expression system using an efficient and novel gene amplification method in mammalian cells." Abstracts of the subjects covered by the lectures on the 28th Annual Meeting of the Molecular Biology Society of Japan, 1P-0621, and partial English language translation thereof. Nov. 25, 2004.

Noriaki Shimizu et al., "Gene Amplification in Mammalian Cells—Its Mechanism and the Product's Behavior." The 51st NIBB Conference, New Aspects of Gene Amplification—Mechanisms and Biological Function, p. 33. Oct. 17, 2005.

Naoyuki Hanada et al., "A Novel, Convenient and Efficient Gene Amplification System in Mammalian Cells—Its application to Recombinant Protein Production." The 51st NIBB Conference, New Aspects of Gene Amplification—Mechanisms and Biological Function, p. 52. Oct. 17, 2005.

DiSanto, J., et al. (1988), "Laboratory Methods, λPMV: A bacteriophage vector allowing single-step retrieval of cDNAs following expression in mammalian cells", *DNA*, 7: 735-741.

Srivatsan, E.S., et al. (1984), "Plasmid, phage, and genomic DNA-mediated transfer and expression of prokaryotic and eukaryotic genes in cultured human cells", *Cytogenet, Cell Genet.* 38: 227-234.

Office Action dated Oct. 13, 2010 issued in U.S. Appl. No. 11/667,963.

Office Action dated Aug. 5, 2013 issued in U.S. Appl. No. 11/667,963.

Office Action dated Dec. 11, 2013 issued in U.S. Appl. No. 11/667,963.

Office Action dated Apr. 11, 2014 issued in U.S. Appl. No. 11/667,963.

* cited by examiner

SEQUENCE LISTING

<160> NUMBER OF SEQ ID NOS: 1

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1
gcgcggccgc ataacttcgt atagcataca ttatacgaag ttatgcggcc gcgc         54

METHOD AND KIT FOR EXPRESSING PROTEIN UNDER REGULATION OF THE EXPRESSION FROM REPEATED SEQUENCE FORMED BY GENE AMPLIFICATION, AND TRANSFORMANT

PRIORITY STATEMENT

The present application is a continuation of pending prior U.S. application Ser. No. 11/667,963 filed on May 14, 2007, which claims priority under 35 U.S.C. §119 to Japan Application No. 2004-334984 filed Nov. 18, 2004 and Japan Application No. 2005-121431 filed Apr. 19, 2005, and which is the national phase under 35 U.S.C. §371 of PCT Application No. PCT/JP2005/020972 filed Nov. 15, 2005, the entire contents of each of which are hereby incorporated herein by reference.

TECHNICAL FIELD

The present invention relates to a method of expressing a protein, whose expression is repressed, from a repeated sequence formed in mammalian cells in which gene amplification is induced.

BACKGROUND ART

The inventor of the present invention has found that it becomes possible to copy a gene (target gene), which encodes a target protein, in an intercellular copy number increased to approximately 100,000 copies simply by plasmid conduction into human-derived cancer cells (COLO 320 colon cancer cell line, and HeLa cell line) by lipofection, the plasmid (hereinafter, "IR/MAR plasmid") having mammalian copying initiation region (IR; initiation region) and a matrix attachment region (MAR; matrix attachment region), and selecting by utilizing a gene tolerance to a chemical (Blasticidin or Neomycin), and that the mass amplification of the target gene can be attained regardless of whether the target gene has a gene structure identical to that of the IR/MAR plasmid (i.e., the target gene has a cis gene structure) or the target gene has a gene structure different from that of the IR/MAR plasmid (i.e., the target gene has a trans gene structure) (see Patent Document 1, Patent Document 2, Non-Patent Document 1, and Non-Patent Document 2).

A cell line in which an IR/MAR plasmid and a target gene were transfected, was analyzed quantitatively as to a transcription amount of mRNA from the target gene. This analysis found that the transcription amount of mRNA was not increased while the copy number of the target gene was increased. It was deduced that the transcription was repressed due to a repeated sequence produced by the mass amplification of a region including the target gene.

One known method of releasing the transcription repression caused by the repeated gene sequence is, for example, treating the cells with histone acetylating enzyme inhibitor such as trichostatin A (see Non-Patent Document 3).

[Patent Document 1]
Japanese Unexamined Patent Application Publication, Tokukai, No. 2003-245083 (published on Sep. 2, 2003)

[Patent Document 2]
Japanese Unexamined Patent Application Publication, Tokukai, No. 2004-337066 (published on Dec. 2, 2004)

[Non-Patent Document 1]
Noriaki Shimizu, et al. (2001) Plasmids with a Mammalian Replication Origin and a Matrix Attachment Region Initiate the Event Similar to Gene Amplification. Cancer Research vol. 61, no. 19, p 6987-6990.

[Non-Patent Document 2]
Noriaki Shimizu, et al (2003) Amplification of plasmids containing a mammalian replication initiation region is mediated by controllable conflict between replication and transcription. Cancer Research, vol. 63, no. 17, p 5281-5290.

[Non-Patent Document 3]
McBurney, M. W. et al, Exp Cell Res (2002), vol 274, p 1-8

Therefore, there is such a problem in that even if a polynucleotide containing the amplified target gene is amplified in order to mass-produce a protein via the amplification of the target gene, the transcription of the target gene is repressed once the repeated sequence is created thereby failing to express the protein of the final target.

Sole application of the method of treating the cells with histone acetylating enzyme inhibitor such as trichostatin A as disclosed in Non-Patent Document 3 could not sufficiently release the transcription repression caused by the repeated sequence of the gene amplified to several thousand to approximately 10 thousand copies.

An object of the present invention is to provide a method and kit etc. for releasing the transcription repression caused by the repeated sequence of the gene, and to establish a system for mass production of useful protein by gene amplification.

DISCLOSURE OF INVENTION

In order to attain the object, the inventor of the present invention diligently worked to find a method capable of amplifying a target gene by using the IR/MAR plasmid, and expressing a protein without transcription repression, even in case where repeated sequence occurs. The inventor accomplished the present invention based on the result of the diligent work.

In order to attain the object, a method according to the present invention is a method of expressing a protein from a repeated sequence formed in mammalian cells in which gene amplification is induced, the protein having been under expression repression, the method including: transfecting a first polynucleotide and a second polynucleotide simultaneously into the mammalian cells, where the first polynucleotide includes an origin of replication and a nuclear matrix attachment region that function in eukaryotic cells, and the second polynucleotide encodes a protein to be expressed, the method further comprising: transfecting at least one of a third polynucleotide and a fourth polynucleotide into the mammalian cells in transfecting the first polynucleotide and the second polynucleotide into the mammalian cells, where the third polynucleotide has a length of 10 kbp or more, and the fourth polynucleotide includes an insulator sequence.

Moreover, in order to attain the object, a method according to the present invention is a method of expressing a protein from a repeated sequence formed in mammalian cells in which gene amplification is induced, the protein having been under expression repression, the method including: transfecting a first polynucleotide and a fifth polynucleotide simultaneously in the mammalian cells, where the first polynucleotide includes an origin of replication and a nuclear matrix attachment region that function in eukaryotic cells, and the fifth polynucleotide includes a second polynucleotide and a chemical tolerance gene, the second polynucleotide encoding a protein to be expressed, the method further comprising: culturing the mammalian cells sequentially in a medium of increasing concentrations of a chemical.

Moreover, in order to attain the object, a method according to the present invention is a method of expressing a protein from a repeated sequence formed in mammalian cells in which gene amplification is induced, the protein having been under expression repression, the method including: transfecting a first polynucleotide and a sixth polynucleotide simultaneously in the mammalian cells where the first polynucleotide includes an origin of replication and a nuclear matrix attachment region that function in eukaryotic cells, and the sixth polynucleotide includes a promoter region and a second polynucleotide controllably linked with each other, the second polynucleotide encoding a protein to be expressed, the method further comprising: transfecting into the mammalian cells a seventh polynucleotide, which encodes a transcription activation factor of the promoter, and expressing the transcription activation factor.

Moreover, in order to attain the object, a method according to the present invention is a method of expressing a protein from a repeated sequence formed in mammalian cells in which gene amplification is induced, the protein having been under expression repression, the method including: transfecting a first polynucleotide and an eighth polynucleotide simultaneously in the mammalian cells, where the first polynucleotide includes an origin of replication and a nuclear matrix attachment region that function in eukaryotic cells, and the eighth polynucleotide includes LoxP gene and a second polynucleotide encoding a protein to be expressed, the method further comprising: transfecting into the mammalian cells a ninth polynucleotide, which includes Cre Recombinase gene, and expressing the Cre Recombinase gene.

Moreover, in order to attain the object, a method according to the present invention is a method of expressing a protein from a repeated sequence formed in mammalian cells in which gene amplification is induced, the protein having been under expression repression, the method including: transfecting a first polynucleotide and a second polynucleotide simultaneously into the mammalian cells, where the first polynucleotide includes an origin of replication and a nuclear matrix attachment region that function in eukaryotic cells, and the second polynucleotide encodes a protein to be expressed, the method further comprising: treating the mammalian cells with 5-aza-2'-deoxycytidine.

Moreover, in order to attain the object, a method according to the present invention is a method of expressing a protein from a repeated sequence formed in mammalian cells in which gene amplification is induced, the protein having been under expression repression, the method comprising: treating the mammalian cells with 5-aza-2'-deoxycytidine.

Moreover, in order to attain the object, a method according to the present invention is a method of expressing a protein from a repeated sequence formed in mammalian cells in which gene amplification is induced, the protein having been under expression repression, the method including: transfecting a first polynucleotide and a second polynucleotide simultaneously into the mammalian cells, where the first polynucleotide includes an origin of replication and a nuclear matrix attachment region that function in eukaryotic cells, and the second polynucleotide encodes a protein to be expressed, the method further comprising: selecting mammalian cells that the gene amplification occurs on a double minute chromosome.

Moreover, in order to attain the object, a method according to the present invention is a method of expressing a protein from a repeated sequence formed in mammalian cells in which gene amplification is induced, the protein having been under expression repression, the method comprising: selecting mammalian cells that the gene amplification occurs on a double minute chromosome.

Moreover, in order to attain the object, a method according to the present invention is a method of expressing a protein from a repeated sequence formed in mammalian cells in which gene amplification is induced, the protein having been under expression repression, the method comprising: transfecting a first polynucleotide and a sixth polynucleotide simultaneously in the mammalian cells, where the first polynucleotide includes an origin of replication and a nuclear matrix attachment region that function in eukaryotic cells, and the sixth polynucleotide includes a promoter region and a second polynucleotide controllably linked with each other, the second polynucleotide encoding a protein to be expressed, the method further comprising: transfecting a seventh polynucleotide into the mammalian cells simultaneously in transfecting the first and sixth polynucleotides into the mammalian cells, the seventh polynucleotide encoding a transcription activation factor of the promoter.

Moreover, in order to attain the object, a method according to the present invention is a method of expressing a protein from a repeated sequence formed in mammalian cells in which gene amplification is induced, the protein having been under expression repression, the method including: transfecting a first polynucleotide and a second polynucleotide simultaneously into the mammalian cells, where the first polynucleotide includes an origin of replication and a nuclear matrix attachment region that function in eukaryotic cells, and the second polynucleotide encodes a protein to be expressed, the method further comprising: selecting mammalian cells that the gene amplification occurs on a double minute chromosome; and treating the mammalian cells with 5-aza-2'-deoxycytidine.

Moreover, in order to attain the object, a method according to the present invention is a method of expressing a protein from a repeated sequence formed in mammalian cells in which gene amplification is induced, the protein having been under expression repression, the method including: transfecting a first polynucleotide and a sixth polynucleotide simultaneously in the mammalian cells where the first polynucleotide includes an origin of replication and a nuclear matrix attachment region that function in eukaryotic cells, and the sixth polynucleotide includes a promoter region and a second polynucleotide controllably linked with each other, the second polynucleotide encoding a protein to be expressed, the method further comprising: transfecting into the mammalian cells a seventh polynucleotide simultaneously in transfecting the first polynucleotide and the second polynucleotide into the mammalian cells, the seventh polynucleotide encoding a transcription activation factor of the promoter; and treating the mammalian cells with 5-aza-2'-deoxycytidine.

The methods according to the present invention may be arranged such that the origin of replication is derived from an origin of replication of c-myc locus, dihydrofolate reductase locus, or β-globin locus.

The methods according to the present invention may be arranged such that the nuclear matrix attachment region is derived from a nuclear matrix attachment region of Igκ locus, SV40 initial region, or dihydrofolate reductase locus.

On the other hand, a kit according to the present invention is a kit for expressing a protein from a repeated sequence formed in mammalian cells in which gene amplification is induced, the protein having been under expression repression, the kit comprising: a first polynucleotide including an origin of replication and a nuclear matrix attachment region that function in eukaryotic cells; and at least one of a third polynucleotide and a fourth polynucleotide where the third polynucleotide has a length of 10 kbp or more, and the fourth polynucleotide includes an insulator sequence.

Moreover, a kit according to the present invention is a kit for expressing a protein from a repeated sequence formed in mammalian cells in which gene amplification is induced, the protein having been under expression repression, the kit comprising: a first polynucleotide including an origin of replication and a nuclear matrix attachment region that function in eukaryotic cells; a polynucleotide including a promoter region; and a seventh polynucleotide encoding a transcription activation factor of the promoter.

Moreover, a kit according to the present invention is a kit for expressing a protein from a repeated sequence formed in mammalian cells in which gene amplification is induced, the protein having been under expression repression, the kit comprising: a first polynucleotide including an origin of replication and a nuclear matrix attachment region that function in eukaryotic cells; a polynucleotide including LoxP gene; and a ninth polynucleotide including Cre Recombinase gene.

The kits according to the present invention preferably further include 5-aza-2'-deoxycytidine.

Moreover, the kits according to the present invention may be arranged such that the origin of replication is derived from an origin of replication of c-myc locus, dihydrofolate reductase locus, or β-globin locus.

Moreover, the kits according to the present invention may be arranged such that the nuclear matrix attachment region is derived from a nuclear matrix attachment region of Igx locus, SV40 initial region, or dihydrofolate reductase locus.

Meanwhile, a transformant according to the present invention is a transformant prepared by inserting into mammalian cells: a first polynucleotide including an origin of replication and a nuclear matrix attachment region that function in eukaryotic cells; a second polynucleotide encoding a protein to be expressed; and at least one of a third polynucleotide and a fourth polynucleotide, where the third polynucleotide has a length of 10 kbp or more, and the fourth polynucleotide includes an insulator sequence.

Moreover, a transformant according to the present invention is a transformant prepared by inserting into mammalian cells: a first polynucleotide including an origin of replication and a nuclear matrix attachment region that function in eukaryotic cells; a sixth polynucleotide includes a promoter region and a second polynucleotide controllably linked with each other, the second polynucleotide encoding a protein to be expressed; and a seventh polynucleotide encoding a transcription activation factor of the promoter.

Moreover, a transformant according to the present invention is a transformant prepared by transfecting into mammalian cells: a first polynucleotide including an origin of replication and a nuclear matrix attachment region that function in eukaryotic cells; an eighth polynucleotide including LoxP gene and a second polynucleotide encoding a protein to be expressed; and a ninth polynucleotide including Cre Recombinase gene, and expressing the Cre Recombinase gene.

Moreover, the transformants according to the present invention may be arranged such that the origin of replication is derived from an origin of replication of c-myc locus, dihydrofolate reductase locus, or β-globin locus.

Moreover, the transformants according to the present invention may be arranged such that the nuclear matrix attachment region is derived from a nuclear matrix attachment region of Igx locus, SV40 initial region, or dihydrofolate reductase locus.

Furthermore, the transformants according to the present invention may be arranged such that the mammalian cells are cells selected from the group consisting of COLO 320DM cells, COLO 320HSR cells, HeLa cells, and CHO cells.

According to the present invention, a protein that has been under expression repression can be expressed from a repeated sequence formed in mammalian cells in which gene amplification is induced. Therefore, the present invention makes it possible to establish a mass production system for a useful protein by employing a gene amplification technique.

For a fuller understanding of the nature and advantages of the invention, reference should be made to the ensuing detailed description taken in conjunction with the accompanying drawings.

added in a medium where clone 9 was obtained in Example 7 and the analysis was carried out by using a cell sorter.

FIG. 14(c) is a view illustrating the result of analysis on the level of the expression of d2EGFP in clone 9 after the expression of d2EGFP was induced with Doxycycline and one-week incubation with 5-aza (final concentration of 3 μM) added in a medium where clone 9 was obtained in Example 7 and the analysis was carried out by using a cell sorter.

Figure 15:
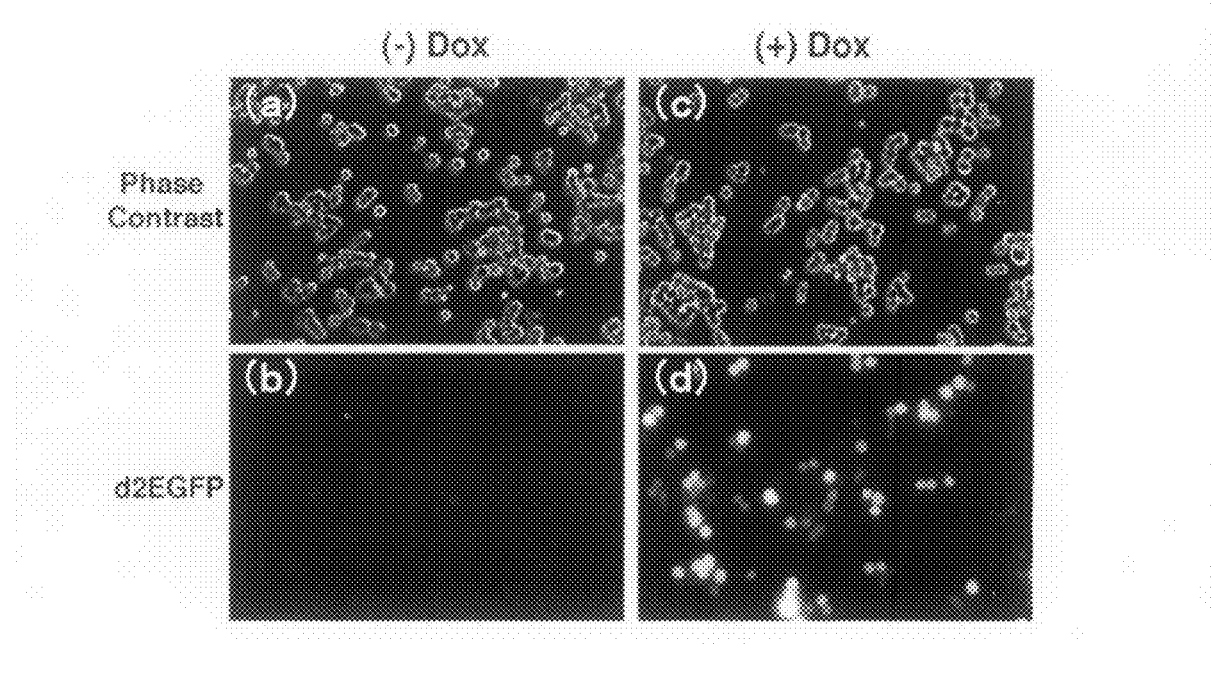

FIG. 15 are phase contrast microscopic images and fluorescence microscopic images of a polyclonal population of transformed cells before and after induction of the expression of d2EGFP with Doxycycline, where the transformed cells were obtained by transfecting pSFVdhfr/d2EGFP and pTet-ON plasmid simultaneously in human colon cancer COLO 320DM cells in Example 8. FIG. 15(a) is a phase contrast microscopic image (×200) before the addition of Doxycycline. FIG. 15(b) is a fluorescence microscopic image (×200) before the addition of Doxycycline. FIG. 15(c) is a phase contrast microscopic image (×200) after the addition of Doxycycline. FIG. 15(d) is a fluorescence microscopic image (×200) after the addition of Doxycycline.

FIG. 16(a) is a view illustrating the result of analysis on the level of the expression of d2EGFP in the polyclonal population of transformed cells before induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(b) is a view illustrating the result of analysis on the level of the expression of d2EGFP in the polyclonal population of transformed cells after 1-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(c) is a view illustrating the result of analysis on the level of the expression of d2EGFP in the polyclonal population of transformed cells after 3-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(d) is a view illustrating the result of analysis on the level of the expression of d2EGFP in the polyclonal population of transformed cells after 6-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(e) is a view illustrating the result of analysis on the level of the expression of d2EGFP in the polyclonal population of transformed cells after 15-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(f) is a view illustrating the result of analysis on the level of the expression of d2EGFP in the polyclonal population of transformed cells after 24-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(g) is a view illustrating the result of analysis on the level of the expression of d2EGFP in the polyclonal population of transformed cells after 48-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(h) is a view illustrating the result of analysis on the level of the expression of d2EGFP in the polyclonal population of transformed cells after 120-hour induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(i) is a view illustrating the result of analysis on the level of the expression of d2EGFP in the polyclonal population of transformed cells after 2-week induction of the expression of d2EGFP with Doxycycline, where the transformed cells were obtained by transfecting pSFVdhfr/d2EGFP and pTet-ON plasmid simultaneously in the human colon cancer COLO 320DM cells and the analysis was carried out by using the cell sorter in Example 8.

FIG. 16(j) is a view illustrating the result of analysis on the level of the expression of d2EGFP in a polyclonal population of a negative control after induction of the expression of d2EGFP with Doxycycline in Example 8, where the analysis was carried out by using the cell sorter.

Figure 17:
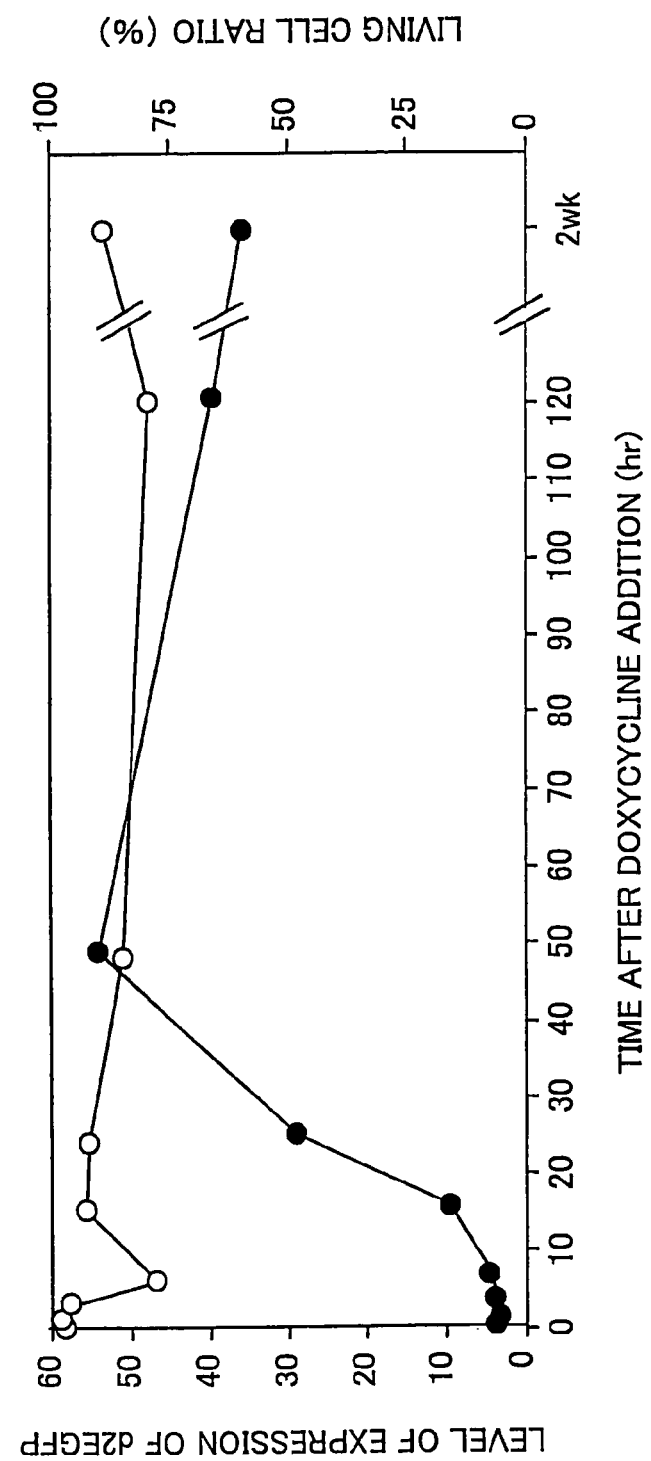

FIG. 17 is a chart in which averages of the levels of the expression of d2EGFP and living cell ratios are plotted against time for the polyclonal population of the transformed cells obtained by simultaneously transfecting pSFVdhfr/d2EGFP and the pTet-ON plasmid into the human colon cancer COLO 320DM cells in Example 8.

FIG. 18(a) is a view illustrating the result of analysis on the level of the expression of d2EGFP in clone A before the induction of the expression in Example 8, where clone A is a given clone selected from among the polyclonal population of the transformed cells obtained by transfecting pSFVdhfr/d2EGFP and pTet-ON plasmid simultaneously in the human colon cancer COLO 320DM cells and the analysis was carried out by using the cell sorter.

FIG. 18(b) is a view illustrating the result of analysis on the level of the expression of d2EGFP in clone A after the induction of the expression in Example 8, where clone A is a given clone selected from among the polyclonal population of the transformed cells obtained by transfecting pSFVdhfr/d2EGFP and pTet-ON plasmid simultaneously in the human colon cancer COLO 320DM cells and the analysis was carried out by using the cell sorter.

FIG. 18(c) is a view illustrating the result of analysis on the level of the expression of d2EGFP in clone B before the induction of the expression in Example 8, where clone B is a given clone selected from among the polyclonal population of the transformed cells obtained by transfecting pSFVdhfr/d2EGFP and pTet-ON plasmid simultaneously in the human colon cancer COLO 320DM cells and the analysis was carried out by using the cell sorter.

FIG. 18(d) is a view illustrating the result of analysis on the level of the expression of d2EGFP in clone B after the induction of the expression in Example 8, where clone B is a given clone selected from among the polyclonal population of the transformed cells obtained by transfecting pSFVdhfr/d2EGFP and pTet-ON plasmid simultaneously in the human colon cancer COLO 320DM cells and the analysis was carried out by using the cell sorter.

FIG. 18(e) is a view illustrating the result of analysis on the level of the expression of d2EGFP in clone C before the induction of the expression in Example 8, where clone C is a given clone selected from among the polyclonal population of the transformed cells obtained by transfecting pSFVdhfr/d2EGFP and pTet-ON plasmid simultaneously in the human colon cancer COLO 320DM cells and the analysis was carried out by using the cell sorter.

FIG. 18(f) is a view illustrating the result of analysis on the level of the expression of d2EGFP in clone C after the induction of the expression in Example 8, where clone C is a given clone selected from among the polyclonal population of the transformed cells obtained by transfecting pSFVdhfr/d2EGFP and pTet-ON plasmid simultaneously in the human colon cancer COLO 320DM cells and the analysis was carried out by using the cell sorter.

Figure 19:
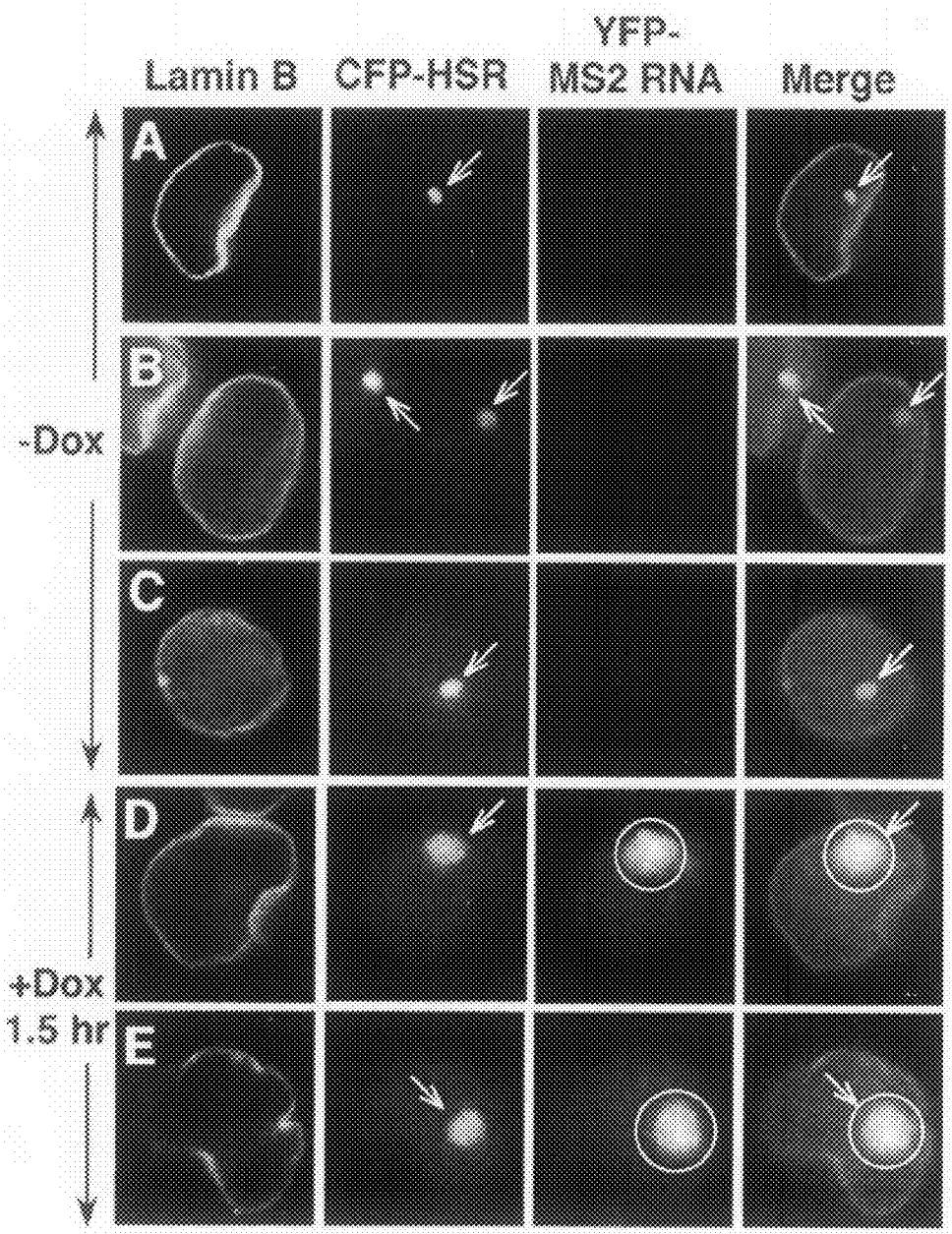

FIG. 19 is a fluorescence microscopic image illustrating that implementation of the method according to Example 8 activated transcription of RNA from an amplified gene on heterochromatized HSR.

FIG. 20(a) is a fluorescence microscopic image illustrating the result of detection of a base sequence of pSFVdhfr/d2EGFP plasmid transfected in a HSR clone isolated in Example 9, where the detection was carried out by the FISH method.

FIG. 20(b) is a fluorescence microscopic image illustrating the result of detection of a base sequence of pSFVdhfr/d2EGFP plasmid transfected in a DM clone isolated in Example 9, where the detection was carried out by the FISH method.

FIG. 21(a) is a fluorescence microscopic image illustrating the result of analysis on the expression of d2EGFP in the isolated HSR clone after 2-day induction of the expression of d2EGFP with Doxycycline in Example 9, where the analysis was carried out by the cell sorter.

FIG. 21(b) is a fluorescence microscopic image illustrating the result of analysis on the expression of d2EGFP in the isolated DM clone (not treated with 5-aza) after 2-day induction of the expression of d2EGFP with Doxycycline in Example 9, where the analysis was carried out by the cell sorter.

FIG. 21(c) is a fluorescence microscopic image illustrating the result of analysis on the expression of d2EGFP in the isolated DM clone (treated with 5-aza) after 2-day induction of the expression of d2EGFP with Doxycycline in Example 9, where the analysis was carried out by the cell sorter.

FIG. 21(d) is a bar graph illustrating accumulated fluorescence intensities in a negative control, the HSR clone, and DM clones (treated and not treated with 5-aza) 2 days after the addition of Doxycycline.

FIG. 22(a) is a fluorescence microscopic image illustrating the result of detection of a base sequence of pSFVdhfr/d2EGFP plasmid transfected in an isolated HSR clone in CHO cells in Example 10, where the detection was carried out by the FISH method.

FIG. 22(b) is a fluorescence microscopic image illustrating the result of detection of a base sequence of pSFVdhfr/d2EGFP plasmid transfected in an isolated DM clone in CHO cells in Example 10, where the detection was carried out by the FISH method.

Figure 23:
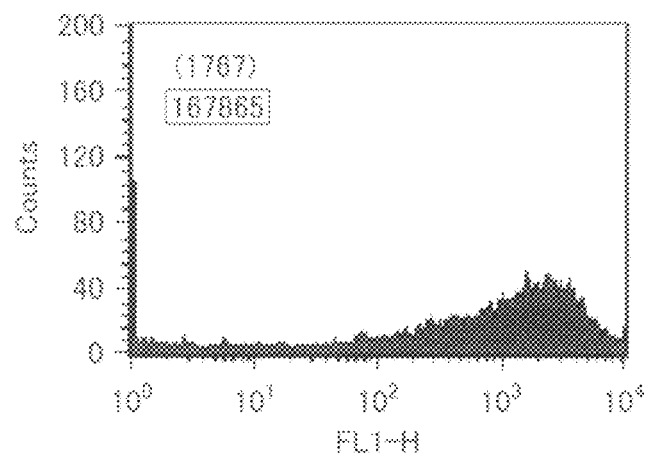
Figure 23:
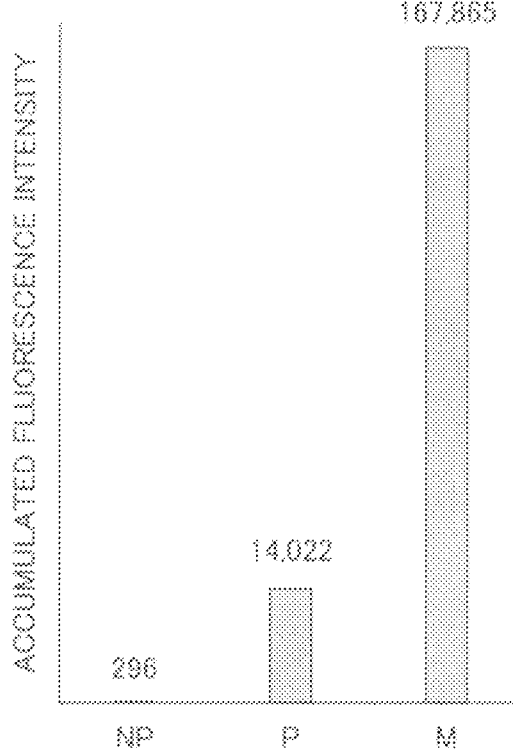
Figure 23:
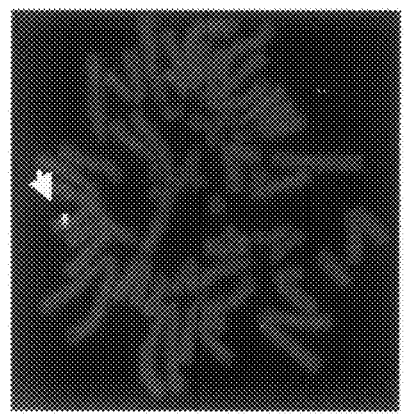

FIG. 23(a) is a view illustrating the result of analysis on the expression of d2EGFP in the isolated max clone (treated with 5-aza) after 2-day induction of the expression of d2EGFP with Doxycycline in Example 10, where the analysis was carried out by the cell sorter.

FIG. 23(b) is a bar graph illustrating accumulated fluorescence intensities of a polyclonal population of transformed cells as a negative control, a polyclonal population of transformed cells of Example 10, and max clone in Example 10.

FIG. 23(c) is a fluorescence microscopic image illustrating the result of detection of a base sequence of pSFVdhfr/d2EGFP plasmid transfected in the max clone isolated in Example 10, where the detection was carried out by the FISH method.

BEST MODE FOR CARRYING OUT THE INVENTION

Embodiments of the present invention are described below. It should be noted that the present invention is not limited thereto.

The present invention is directed to a method of expressing a protein from a repeated sequence formed in mammalian cells in which gene amplification is induced, the protein having been under expression repression. Here, what is meant by the term "repeated sequence" is a base sequence in which one unit base sequence is repeated. It is known that there is a case that the presence of such a repeated sequence causes heterochromatization in a gene region in which it is present, thereby repressing the gene transcription.

As described above, the inventor of the present invention has found that it becomes possible to copy a gene (target gene), which encodes a target protein, in an intercellular copy number increased to approximately 100,000 copies simply by plasmid conduction into human-derived cancer cells (COLO 320 colon cancer cell line, and HeLa cell line) by lipofection, the plasmid (hereinafter, "IR/MAR plasmid") having mammalian copying initiation region (IR; initiation region) and a matrix attachment region (MAR; matrix attachment region), and selecting by utilizing a chemical-tolerance gene (Blasticidin or Neomycin), and that the mass amplification of the target gene can be attained regardless of whether the target gene has a gene structure identical to that of the IR/MAR plasmid (i.e., the target gene has a cis gene structure) or the target gene has a gene structure different from that of the IR/MAR plasmid (i.e., the target gene has a trans gene structure) (see Patent Document 1, Patent Document 2, Non-Patent Document 1, and Non-Patent Document 2).

Therefore, it was found that a mass gene amplification system does not show an increase in transcription of Blasticidin resistance gene (target gene) in mRNA even if a copy number of the Blasticidin resistance gene is increased. It is deduced that this phenomenon was due to transcription repression by the repeated sequence produced as a result of the mass amplification of a gene region including the target gene. The present invention is accomplished to express an expression-repressed protein by (a) releasing the transcription repression caused by such a repeated sequence, or (b) selecting cells (clones) in which the transcription repression does not occur (or a degree of the transcription repression is low), out of a cell population (clone population) in the majority of which the transcription repression occurs.

Therefore, in the present invention, the term "method of expressing a protein that has been under expression repression" encompasses not only methods of expressing an expression-repressed protein by releasing transcription repression caused by a repeated sequence, but also methods of expressing a desired protein by selecting cells (clones) in which the transcription repression does not occur (or a degree of the transcription repression is low), out of a cell population (clone population) in the majority of which the transcription repression occurs.

In the present invention, what is meant by the term "mammalian cells in which gene amplification is induced" is mammalian cells in which amplification of a gene (polynucleotide) is induced. One example of such mammalian cells is mammalian cells in which the above-described IR/MAR plasmid is conducted. The mammalian cells are not particularly limited. For example, the mammalian cells may be CHO-K1 cells (available as e.g., ATCC CCL-61, RIKEN RCB0285, RIKEN RCB0403, etc.). However, it is especially preferable that the mammalian cells be tumor cells having an infinite proliferation ability. Examples of such tumor cells encompass HeLa cells (available as e.g., ATCC CCL-2, ATCC CCL-2.2, RIKEN RCB0007, RIKEN RCB0191 etc.), human colon cancer COLO 320DM cells (derived from, e.g., ATCC CCL-220), human colon cancer COLO 320HSR cells (available as e.g., ATCC CCL-220.1), NSO cells (available as e.g., RIKEN RCB0213), and the like.

Embodiment 1

A method according to the present embodiment includes transfecting a first polynucleotide and a second polynucleotide simultaneously into mammalian cells in which the gene amplification is induced, where the first polynucleotide includes an origin of replication and a nuclear matrix attachment region that function in eukaryotic cells, and the second polynucleotide encodes a protein to be expressed, the method further including transfecting at least one of a third polynucleotide and a fourth polynucleotide into the mammalian cells in transfecting the first polynucleotide and the second polynucleotide into the mammalian cells, where the third polynucleotide has a length of 10 kbp or more, and the fourth polynucleotide includes an insulator sequence.

The first polynucleotide includes an origin of replication and a nuclear matrix attachment region that function in the eukaryotic cells. The origin of replication included in the first polynucleotide is not particularly limited, provided that the origin of replication functions in eukaryotic cells. Examples of the origin of replication encompass c-myc locus, dihydrofolate reductase locus, β-globin locus, etc. The c-myc locus is described for example in "McWhinney, C. et al., Nuclear Acids Res. vol. 18, p 1233-1242 (1990)". The dihydrofolate reductase locus is described for example in "Dijkwel, P. A. et al., Mol. Cell. Biol. vol. 8, p 5398-5409 (1988)". β-globin locus is described for example in "Aladjem, M. et al., Science vol. 281, p 1005-1009 (1998)".

The nuclear matrix attachment region included in the first polynucleotide is not particularly limited, provided that the nuclear matrix attachment region functions in eukaryotic cells. Examples of the nuclear matrix attachment region encompass sequences derived from a nuclear matrix attachment region of a locus such as Igx locus, SV40 initial region, dihydrofolate reductase locus, or the like. The nuclear matrix attachment region of the Igx locus is described for example in Tsutsui, K. et al., J. Biol. Chem. vol. 268, p 12886-12894 (1993). The nuclear matrix attachment region of the SV40 initial region is described for example in Pommier, Y. et al., J. Virol., vol 64, p 419-423 (1990). The nuclear matrix attachment region of dihydrofolate reductase locus is described for example in Shimizu N. et al., Cancer Res. vol. 61, p 6987-6990.

If necessary for its purposes, the first polynucleotide may include a sequence necessary for cloning in *Escherichia coli*, or a selection marker such as a chemical-tolerance gene (Blasticidin resistance gene, Neomycin resistance gene, etc.), green fluorescent protein gene or the like, as a marker protein, in addition of the origin of replication and nuclear matrix attachment region. The selection marker can be used as an indicator to select the cells in which the first polynucleotide is transfected.

Meanwhile, the second polynucleotide is a polynucleotide for encoding the protein to be expressed (such a polynucleotide is referred to as a "gene (for) encoding a target protein" where appropriate). The second polynucleotide is not particularly limited and a polynucleotide encoding a desired protein can be appropriately selected to employ. The polynucleotide can be obtained based on its basic sequence information by using a known method such as PCR. In the explanation of the present invention, the "protein to be expressed" is referred to as the "target protein".

By simultaneously transfecting, into the mammalian cells, the first polynucleotide and the second polynucleotide that encodes the protein to be expressed, the "mass gene amplification system" disclosed in Patent Document 1 etc. by the inventor of the present invention can be constructed, and the cells can amplify the second polynucleotide. The mammalian cells in which the first and second nucleotides are simultaneously transfected are "mammalian cells in which the gene amplification is induced" as termed in the present invention. The mammalian cells to which the first and second polynucleotides are to be transfected is not particularly limited, and may be CHO cells or the like. It is however especially preferable that the mammalian cells be tumor cells that have infinite proliferation ability. Examples of the tumor cells encompass HeLa cells, human colon cancer COLO 320DM cells, human colon cancer COLO 320HSR cells, NSO cells, etc. The human colon cancer COLO 320DM cells and human colon cancer COLO 320HSR cells are described for example in Quinn, L. A., Moore, G. E., Morgan, R. T., and Woods, L. K. Cell lines from human colon carcinoma with unusual cell products, double minutes, and homogeneously staining regions. Cancer Res. 1979 39(12):4914-4924. and in Shimizu, N., Kanda, T., and Wahl, G. M. Selective capture of acentric fragments by micronuclei provides a rapid method of purifying extrachromosomally amplified DNA. Nat. Genet., 12: 65-71, 1996.

The transfection of the first and second polynucleotide into the cell is not particularly limited, provided that both the polynucleotides are thereby transfected simultaneously into the mammalian cells. Both the polynucleotides may be transfected therein as one gene structure in which both the polynucleotides are linked, or as different gene structures. The form of the gene structure may be a plasmid or a cosmid.

The first and second polynucleotides may be transfected into the cells by any method, which may be a known method such as lipofection, electroporation, particle-gun, etc.

In such mammalian cells in which the first and second polynucleotides are transfected, the amplification of the second polynucleotide produces a repeated sequence, which causes transcription repression, resulting in repression of protein expression. The inventor of the present invention compared this phenomenon with a repeated sequence that occurs in gene amplification of carcinogenesis process ("Reference Example 1" described later). The comparison showed that the transcription of mRNA having a gene amplification region caused in the carcinogenesis process was not repressed. A repeated sequence produced by a plasmid (pSFVdhfr) having an IR and an MAR, which was shown in Comparative Example 1, is different from the repeated sequence produced in the carcinogenesis process in that the sequence repeated in the latter was long (usually, 100 to 200 kbp), and the repeated sequence of the latter was complicated as a result of recombination and the like. Therefore, the results of Comparative Example 1 and Reference Example 1 suggest that a longer repeating unit and more complicated repeated structure would increase transcription of the repeated sequence produced by the plasmid having IR and MAR to mRNA.

A method according to the present embodiment was established based on this study. More specifically, the method according to the present embodiment includes transfecting at least one of the third polynucleotide and the fourth polynucleotide into the mammalian cells in transfecting the first nucleotide and the second nucleotide into the mammalian cells, where the third polynucleotide has a length of 10 kbp or more, and the fourth polynucleotide includes an insulator sequence.

By transfecting the third polynucleotide into the mammalian cells simultaneously with the transfection of the first and second polynucleotides therein, the polynucleotide encoding the protein to be expressed and the third polynucleotide are coamplified. Consequently, the repeated sequence is formed with a long repeating unit or a complicated structure by the amplification of the polynucleotide (gene). This releases the transcription repression caused by the repeated sequence, thereby making it possible to express the protein as much as the polynucleotides are copied.

The length of the third polynucleotide is preferably 10 kbp or longer, more preferably 50 kbp or more, and most preferably 100 kbp or more. The third polynucleotide is not particularly limited in terms of its basic sequence, provided that the third polynucleotide satisfies the requirement of the length. The third polynucleotide may be a polynucleotide encoding a protein or a polynucleotide not encoding a protein. The third polynucleotide may be prepared appropriately by synthesis or the other method, or may be selected appropriately from among known polynucleotides such as 2-phage DNA, human genome DNA, etc.

On the other hand, by transfecting the fourth polynucleotide into the mammalian cells simultaneously with the transfection of the first and second polynucleotides therein, the polynucleotide encoding the protein to be expressed and the polynucleotide having the insulator sequence are coamplified. Consequently, the repeated sequence is formed with a long repeating unit or a complicated structure by the amplification of the polynucleotide (gene). Further, heterochromatization will not be spread around. This releases the transcription repression caused by the repeated sequence, thereby making it possible to express the protein as much as the polynucleotides are copied.

Here, the "insulator sequence" is a boundary of chromatin, and it is known that the insulator sequence is a DNA sequence independent of the gene expression. Examples of the insulator sequence encompass HS4 insulator sequence derived from Aves (1210 bp, see "Recillas-Targa, F. et al., Proc. Natl. Acad. Sci. U.S.A., vol. 99, p 6883-6888, (2002)"), ARS insulator sequence derived from Echinoidea (575 bp, "Akasaka K, et al., Cell. Mol. Biol. vol. 45, p 555-565 (1999).").

Into the mammalian cells, the third or fourth polynucleotide and the first or second polynucleotide may be transfected as a gene structure or different gene structures. Because the third or fourth polynucleotide is relatively large in size, and the transfection of one gene structure including the third or fourth polynucleotide and first or second polynucleotide into the mammalian cells further requires transfecting the third or fourth polynucleotide into a gene structure including the first or second polynucleotide, it is preferable that the third or fourth polynucleotide and the first or second polynucleotide be transfected as different gene structures. For attaining greater releasing of the transcription repression, it is preferable to transfect both of the third and fourth polynucleotides into the mammalian cells, albeit it is sufficient that the third or fourth polynucleotide is transfected therein. As to the form and transfecting method of the gene structure into the mammalian cells, the third and the fourth polynucleotides can be described in the same way as the first and second polynucleotides are described.

The later-described Examples 1 and 2 discuss how effective the method according to the present embodiment is. In Examples 1 and 2, it was confirmed that transcription repression of polynucleotides encoding proteins to be expressed was released whereby the expression of target protein was increased.

The present invention covers a transformant obtained by the method according to the present embodiment.

Embodiment 2

A method according to the present embodiment includes transfecting a first polynucleotide and a fifth polynucleotide simultaneously in the mammalian cells in which the gene amplification is induced, where the first polynucleotide includes an origin of replication and a nuclear matrix attachment region that function in eukaryotic cells, and the fifth polynucleotide includes a second polynucleotide and a chemical tolerance gene, the second polynucleotide encoding a protein to be expressed, the method further including culturing the mammalian cells sequentially in a medium of increasing concentrations of a chemical.

The fifth polynucleotide is a polynucleotide includes the second polynucleotide encoding a protein to be expressed, and a chemical tolerance gene. Examples of the chemical tolerance gene encompass Blasticidin resistance gene, Neomycin resistance gene, Hygromycin tolerance gene, and the like. The transfection of the fifth polynucleotide can be carried out by transfecting into the mammalian cells one gene structure including the fifth polynucleotide and the first or fifth polynucleotide, or by transfecting into the mammalian cells the fifth polynucleotide and the first polynucleotide as different gene structures. As to the form and transfecting method of the gene structure into the mammalian cells, the fifth polynucleotides can be described in the same way as the first and second polynucleotides are described.

The present embodiment includes the mammalian cells, in which the first and fifth polynucleotides are transfected, sequentially in the medium of increasing concentrations of the chemical. In the mammalian cells in which the first and the fifth polynucleotides are transfected, the polynucleotide encoding the protein to be expressed and the chemical tolerance gene are coamplified. By culturing such mammalian cells sequentially in the medium of increasing concentrations of the chemical, mammalian cells in which the transcription repression caused by the repeated sequence does not occur (or a degree of the transcription repression is low) can be selected using the chemical tolerance as an indicator. Therefore, it is possible to select the mammalian cells in which the transcription repression caused by the repeated sequence does not occur (or a degree of the transcription repression is low) for the polynucleotide encoding the protein to be expressed. Thereby, it becomes possible to express the protein as much as this polynucleotide is copied.

The increasing the concentration of the chemicals for the cell culturing can be done in any way. The cells may be passaged in the medium of increasing concentrations of the chemical. As an alternative, the chemical may be added to the medium consequently. More specifically, the former case is preferably arranged such that the cells are incubated in the medium of one concentration for 3 to 7 days and then incubated to the medium of a next concentration. Moreover, the former case is preferably arranged such that an increasing rate of the chemical concentration is in a range of 30 to 100%. The latter case is preferably arranged such that the chemical is added to the medium to increase its concentration by 10% to 30% per 24 hours. In the later-described Example 3, the concentration of a chemical (Blasticidin) was doubled in intervals of 3 to 5 days.

There is no limitation as to an upper limit of the chemical to be added to the medium, because the upper limit is dependent on the kind of the chemical, kind of the cells, and conditions, etc. The upper limit should be determined as appropriate.

The later-described Example 3 discusses how effective the method according to the present embodiment. In Example 3, it was confirmed that transcription repression of a polynucleotide encoding a protein to be expressed was released whereby the expression of the target protein was increased.

Embodiment 3

A method according to the present embodiment includes transfecting a first polynucleotide and a sixth polynucleotide simultaneously in the mammalian cells in which the gene amplification is induced, where the first polynucleotide includes an origin of replication and a nuclear matrix attachment region that function in eukaryotic cells, and the sixth polynucleotide includes a promoter region and a second polynucleotide controllably linked with each other, the second polynucleotide encoding a protein to be expressed, the method further including transfecting into the mammalian cells a seventh polynucleotide, which encodes a transcription activation factor of the promoter, and expressing the transcription activation factor.

The sixth polynucleotide is a polynucleotide including a promoter region and the second polynucleotide controllably linked with each other. The second polynucleotide is a polynucleotide encoding a protein to be expressed. The promoter region is not particularly limited, provided that the promoter region can function in the mammalian cells in which the sixth polypeptide is to be transfected, and transcription of the promoter region can be controlled by the transcription activation factor. For example, the promoter region may be a TRE promoter (Clontech Laboratories Inc.), T-REX promoter (Invitrogen Corp.), or the like. The transfection of the sixth polynucleotide into the mammalian cells having a gene amplification ability may be carried out by transfecting one gene structure including the sixth polynucleotide and the first polynucleotide, or by transfecting the sixth polynucleotide and the first polynucleotide as different gene structures. As to the form and transfecting method of the gene structure into the mammalian cells, the sixth polynucleotides can be described in the same way as the first and second polynucleotides are described.

The present embodiment includes transfecting into the mammalian cells the seventh polynucleotide, which encodes a transcription activation factor of the promoter, and expressing the transcription activation factor. By this step, it is possible to encourage the activation of the promoter that controls the expression of the protein to be expressed. This makes it possible to express the protein that has been under the expression repression by the repeated sequence. The seventh polynucleotide is a polynucleotide that encodes the transcription activation factor of the promoter included in the sixth polynucleotide. For example, if the promoter was a TRE promoter, the seventh polynucleotide might be Tet-ON gene (Clontech Laboratories Inc.).

In transfecting the seventh polynucleotide into the mammalian cells and expressing the transcription activation factor, the transfection of the seventh polynucleotide may be carried out by one gene structure into the mammalian cells, the gene structure constructed by controllably linking the seventh polynucleotide with a promoter that promotes the expression of the seventh polynucleotide. The promoter for promoting the expression of the seventh polynucleotide is not particularly limited, provided that the promoter can function in mammalian cells. The promoter may be inducible or non-inducible. Moreover, timing of the transfecting the gene structure including the seventh polynucleotide into the mammalian cells may be after or before the transfection of the first and sixth polynucleotides. As to the form and transfecting method of the gene structure into the mammalian cells, the seventh polynucleotides can be described in the same way as the first and second polynucleotides are described.

The later-described Example 4 discusses how effective the method according to the present embodiment. In Example 4, it was confirmed that transcription repression of a polynucleotide encoding a protein to be expressed was released whereby the expression of the target protein was increased.

The present invention covers a transformant obtained by the method according to the present embodiment.

Embodiment 4

A method according to the present embodiment includes transfecting a first polynucleotide and an eighth polynucleotide simultaneously in the mammalian cells in which the gene amplification is induced, where the first polynucleotide includes an origin of replication and a nuclear matrix attachment region that function in eukaryotic cells, and the eighth polynucleotide includes LoxP gene and a second polynucleotide encoding a protein to be expressed, the method further including transfecting into the mammalian cells a ninth polynucleotide, which includes Cre Recombinase gene, and expressing the Cre Recombinase gene.

The eighth polynucleotide is a polynucleotide, which includes the second polynucleotide and the LoxP gene. The LoxP gene is a gene relating to Cre-LoxP system (see "Molecular Cloning—a laboratory manual 3rd Ed.", by J. Sambrook and D. W. Russell, Cold Spring Harbor Laboratory Press (2001), page 4.82-4.85.) The LoxP gene may be provided with a restriction endonuclease recognizing sequence or a restriction endonuclease cleaved sequence on both terminals (5' terminal and 3' terminal).

The ninth polynucleotide is a polynucleotide, which includes Cre Recombinase gene that relates to Cre-LoxP System. The ninth polynucleotide preferably includes a promoter for promoting the expression of the Cre Recombinase gene.

The transfection of the first, eighth, and ninth polynucleotides into the mammalian cells causes amplification of the LoxP gene and the polynucleotide for encoding the protein to be expressed. As a result, Cre Recombinase expressed in the mammalian cells recognizes the LoxP gene and extrachromosomally cleaves the polynucleotide for encoding the protein to be expressed. The cleaved-away polynucleotide forms a cyclic molecule. The extrachromosomal cyclic molecule is hardly susceptible to the transcription repression or the like. Therefore, this avoids the transcriptions caused by the repeated sequence. Thereby, it becomes possible to express the protein as much as this polynucleotide is copied.

As to the transfecting method of the polynucleotides into the mammalian cells, the polynucleotides can be described in the same way as the first and second polynucleotides are described. Moreover, timing of the transfecting, the transfection of the ninth polynucleotide may be after or before the transfection of the first and eighth polynucleotides.

The later-described Example 5 discusses how effective the method according to the present embodiment. In Example 5, it was confirmed that transcription repression of a polynucleotide encoding a protein to be expressed was released whereby the expression of the target protein was increased.

The present invention covers a transformant obtained by the method according to the present embodiment.

Embodiment 5

A method according to the present embodiment includes transfecting a first polynucleotide and a second polynucleotide simultaneously into mammalian cells in which the gene amplification is induced, where the first polynucleotide includes an origin of replication and a nuclear matrix attachment region that function in eukaryotic cells, and the second polynucleotide encodes a protein to be expressed, the method further including treating the mammalian cells with 5-aza-2'-deoxycytidine.

Silencing (transcription repression) of DNA by RNAi is accompanied with methylation of DNA. On this account, the inventor of the present invention uniquely arrived to an idea that the transcription repression can be released by lowering a degree of the methylation of DNA. Because it is known that 5-aza-2'-deoxycytidine lowers the degree of the methylation of DNA, the inventor of the present invention employs 5-aza-2'-deoxycytidine. 5-aza-2'-deoxycytidine may be a commercially available one. For example, 5-aza-2'-deoxycytidine may be purchased from Sigma.

The treatment of the mammalian cells with 5-aza-2'-deoxycytidine may be carried out in any way, provided that the mammalian cells can be in contact with 5-aza-2'-deoxycytidine. For example, the mammalian cells may be cultured in a medium containing 5-aza-2'-deoxycytidine. In this arrangement, different kinds and conditions of the cells have different optimum conditions. Thus, the concentration of 5-aza-2'-deoxycytidine may be set as appropriate. In general, the concentration of 5-aza-2'-deoxycytidine is preferably in a range of 0.2 µM to 10 µM, and more preferably in a range of 1 µM to 2 µM. A concentration of 5-aza-2'-deoxycytidine above the preferable ranges would be toxic to the mammalian cells, while a concentration of 5-aza-2'-deoxycytidine below the preferable ranges could not sufficiently release the transcription repression. The medium to which 5-aza-2'-deoxycytidine is added is not particularly limited, provided that the mammalian cells can be cultured in the medium. For example, the medium may be Dulbecco's modified Eagle's medium (DEM medium: Invitrogen Corp.), RPMI1640 medium (Nissui Pharmaceutical Co., Ltd.), or the like medium. The culturing is carried out with the medium to which 10% fetal bovine serum is added.

Treatment period of the mammalian cells is not particularly limited, because the treatment period is dependent on the concentration of 5-aza-2'-deoxycytidine, the kinds and conditions of the cells. However, it is preferable that the mammalian cells be treated for a period in a range of 3 days to 10 days.

The later-described Example 6 discusses how effective the method according to the present embodiment. In Example 6, it was confirmed that transcription repression of a polynucleotide encoding a protein to be expressed was released whereby the expression of the target protein was increased.

The method including treating the mammalian cells with 5-aza-2'-deoxycytidine is not only applicable to the mammalian cells in which the first and second polynucleotides are transfected, but also to a wide range of mammalian cells in which the gene amplification is induced. For example, this method is also applicable to mammalian cells prepared by simultaneously transfecting (a) a gene encoding a protein and (b) DHFR (Dihydrofolate reductase) gene into CHO (Chinese Hamster Ovary) cells so that the gene amplification becomes possible.

Embodiment 6

A method according to the present embodiment includes transfecting a first polynucleotide and a second polynucleotide simultaneously into mammalian cells in which the gene amplification is induced, where the first polynucleotide includes an origin of replication and a nuclear matrix attachment region that function in eukaryotic cells, and the second polynucleotide encodes a protein to be expressed, the method further including selecting mammalian cells that the gene amplification occurs on a double minute chromosome.

The inventor of the present invention isolated clones expressing a target protein, from among stable transformant cell population of mammalian cells in which a polynucleotide (gene) encoding the target protein and an IR/MAR plasmid. Then, the inventor compared the clones in terms of an amount of the target protein expressed. The comparison demonstrated that the expression of the target protein was increased in a clone in which the amplification of the polynucleotide (gene) encoding the target protein occurred on the extrachromosomal double minute chromosome (hereinafter, referred to as "DM") than in a clone in which the amplification of the polynucleotide (gene) encoding the target protein occurred on a homogeneously staining region (hereinafter, referred to as "HSR") of a chromosome. That is, a clone in which the transcription repression caused by the repeated sequence is not occurred can be selected by selecting a clone in which the amplification of the polynucleotide (gene) encoding a target protein is occurred on DM, from among mammalian cells in which the polynucleotide (gene) is highly amplified by using a mass gene amplification system.

The selecting of the mammalian cells (clone) in which the gene amplification occurs on DM may be carried out by any method. One example of the selecting method is a method including performing a well-known FISH method (fluorescence in situ hybridization) on chromosomes in mitotic phase, detecting any one of the first to ninth polynucleotides transfected in the mammalian cells, and isolating the mammalian cells (clone) having fluorescent DM. HSR is a region on a chromosome, while DM is present out of the chromosome. Thus, mammalian cells (clone) having a fluorescent extrachromosomal region may be select by fluorescence microscope observation. The FISH method is not specifically limited and may be performed in any way. The FISH method may be carried out in a well-known fashion appropriately selected.

As an alternative, another example of the selecting method is a method including embedding Lactose Operator (LacO) sequence in any one of the first to ninth polynucleotides, amplifying the polynucleotide containing Lactose Operator (LacO), and visualizing the polynucleotide containing Lactose Operator (LacO) by expressing Lactose Repressor (LacR)-Green Fluorescent Protein (GFP) fusion gene (see "Kanda, T., and G. M. Wahl. 2000. The dynamics of acentric chromosomes in cancer cells revealed by GFP-based chromosome labeling strategies. J Cell Biochem. Suppl:107-114."; "Li, G., G. Sudlow, and A. S. Belmont. 1998. Interphase cell cycle dynamics of a late-replicating, heterochromatic homogeneously staining region: Precise choreography of condensation/decondensation and nuclear positioning. J. Cell Biol. 140:975-989."; and "Shimizu, N., K. Shingaki, Y. Kaneko-Sasaguri, T. Hashizume, and T. Kanda. 2005. When, where and how the bridge breaks: anaphase bridge breakage plays a crucial role in gene amplification and HSR generation. Exp Cell Res. 302:233-243.").

The followings are known for DM and HSR. Gene amplification is a main system for attaining infinite proliferation-restricting amplification and anti-chemical property of tumor cells (see "Benner, S. E., Wahl, G. M., and Von Hoff, D. D. Double minute chromosomes and homogeneously staining regions in tumors taken directly from patients versus in human tumor cell lines. Anti-Cancer Drugs, 2: 11-25, 1991"). Cytogenetically, the amplified gene is most frequently found on the extrachromosomal double minute chromosome (DM) in vivo. Long in vitro passage, however, dominantly amplifies cells having the amplified gene in a homogeneously staining region (HSR) of a chromosome in general. Previous researches showed that the tumor cells in tumor expressing and cell differentiating states are restored to a normal state by removing the amplified gene on DM therefrom (see "Shimizu, N., Nakamura, H., Kadota, T., Kitajima, K., Oda, T., Hirano, T., and Utiyama, H. Loss of amplified c-myc genes in the spontaneously differentiated HL-60 cells. Cancer Res., 54: 3561-3567, 1994.", "Von Hoff, D. D., McGill, J. R., Forseth, B. J., Davidson, K. K., Bradley, T. P., Van Devanter, D. R., and Wahl, G. M. Elimination of extrachromosomally amplified MYC genes from human tumor cells reduces their tumorigenicity. Proc. Natl. Acad. Sci. USA, 89: 8165-8169, 1992.", and "Eckhardt, S. G., Dai, A., Davidson, K. K., Forseth, B. J., Wahl, G. M., and Von Hoff, D. D. Induction of differentiation in HL60 cells by the reduction of extrachromosomally amplified c-myc. Proc. Natl. Acad. Sci. USA, 91: 6674-6678, 1994."). This kind of removing step is mediated by selective uptake of DM into microcells discharged from dividing cells. (see "Von Hoff, D. D., McGill, J. R., Forseth, B. J., Davidson, K. K., Bradley, T. P., Van Devanter, D. R., and Wahl, G. M. Elimination of extrachromosomally amplified MYC genes from human tumor cells reduces their tumorigenicity. Proc. Natl. Acad. Sci. USA, 89: 8165-8169, 1992.", "Shimizu, N., Kanda, T., and Wahl, G. M. Selective capture of acentric fragments by micronuclei provides a rapid method of purifying extrachromosomally amplified DNA. Nat. Genet., 12: 65-71, 1996.", and "Shimizu, N., Shimura, T., and Tanaka, T. Selective elimination of acentric double minutes from cancer cells through the extrusion of micronuclei. Mutat. Res., 448: 81-90, 2000."). It has been understood that the micronucleation closely relates to behavior of DM in the cells in cell cycle (see "Tanaka, T., and Shimizu, N. Induced detachment of acentric chromatin from mitotic chromosomes leads to their cytoplasmic localization at G1 and the micronucleation by lamin reorganization at S phase. J. Cell Sci., 113: 697-707, 2000."). DM is constituted by acentric cyclic DNAs in various sizes (see "Levan, A., and Levan, G. Have double minutes functioning centromeres? Hereditas, 88: 81-92, 1978."). Although they are acentric, DM can divide and descend stably to daughter cells by attaching to mitotically dividing chromosomes (see "Tanaka, T., and Shimizu, N. Induced detachment of acentric chromatin from mitotic chromosomes leads to their cytoplasmic localization at G1 and the micronucleation by lamin reorganization at S phase. J. Cell Sci., 113: 697-707, 2000.", "Levan, A., and Levan, G. Have double minutes functioning centromeres? Hereditas, 88: 81-92, 1978.", and "Kanda, T., Sullivan, K. F., and Wahl, G. M. Histone-GFP fusion protein enables sensitive analysis of chromosome dynamics in living mammalian cells. Curr. Biol., 8: 377-385, 1998."). Recent important relevant findings showed that similar systems are used in mitosis of some viral nuclear plasmids such as bovine papilloma virus (see "Lehman, C. W., and Botchan, M. R. Segregation of viral plasmids depends on tethering to chromosomes and is regulated by phosphorylation. Proc. Natl. Acad. Sci. USA, 95: 4338-4343, 1998."), EB virus (see "Marechal, V., Dehee, A., Chikhi-Brachet, R., Piolot, T., Coppey-Moisan, M., and Nicolas, J. C. Mapping EBNA-1 domains involved in binding to metaphase chromosomes. J. Virol., 73: 4385-4392, 1999."), Kaposi's sarcoma-associated herpes virus (see "Ballestas, M. E., Chatis, P. A., and Kaye, K. M. Efficient persistence of extrachromosomal KSHV DNA mediated by latency-associated nuclear antigen. Science (Wash. DC), 284: 641-644, 1999."), and SV40 (see "Baiker, A., Maercker, C., Piechaczek, C., Schmidt, S. B., Bode, J., Benham, C., and Lipps, H. J. Mitotic stability of an episomal vector containing a human scaffold/matrix-attached region is provided by association with nuclear matrix. Nature Cell Biol., 2: 182-184, 2000."). Furthermore, a recent interesting research found that a plasmid having EB virus replicon can be embedded into DM in tumor cells (see "Kanda, T., Otter, M., and Wahl, G. M. Mitotic segregation of viral and cellular acentric extrachromosomal molecules by chromosome tethering. J. Cell Sci., 114: 49-58, 2001.).

As to the method of transfecting the first and second polynucleotides into the mammalian cells, and as to the gene structure for transfecting the polynucleotides into the mammalian cells, the present embodiment may be described in the same way as Embodiment 1.

The later-described Example 7 discusses how effective the method according to the present embodiment. In Example 7, it was confirmed that transcription repression of a polynucleotide encoding a protein to be expressed was released whereby the expression of the target protein was increased.

The method according to the present embodiment is not only applicable to the mammalian cells in which the first and second polynucleotides are transfected, but also to a wide range of mammalian cells in which the gene amplification is induced. For example, this method is also applicable to mammalian cells prepared by simultaneously transfecting (a) a gene encoding a protein and (b) DHFR (Dihydrofolate reductase) gene into CHO (Chinese Hamster Ovary) cells so that the gene amplification becomes possible.

Embodiment 7

A method according to the present embodiment includes transfecting a first polynucleotide and a sixth polynucleotide simultaneously in the mammalian cells in which the gene amplification is induced, where the first polynucleotide includes an origin of replication and a nuclear matrix attachment region that function in eukaryotic cells, and the sixth polynucleotide includes a promoter region and a second polynucleotide controllably linked with each other, the second polynucleotide encoding a protein to be expressed, the method further including transfecting a seventh polynucleotide into the mammalian cells simultaneously in transfecting the first and sixth polynucleotides into the mammalian cells, the seventh polynucleotide encoding a transcription activation factor of the promoter.

The sixth polynucleotide is a polynucleotide including a promoter region and the second polynucleotide controllably linked with each other. The second polynucleotide is a polynucleotide encoding a protein to be expressed. The promoter region is not particularly limited, provided that the promoter region can function in the mammalian cells in which the sixth polypeptide is to be transfected, and transcription of the promoter region can be controlled by the transcription activation factor. For example, the promoter region may be a TRE promoter (Clontech Laboratories Inc.), T-REX promoter (Invitrogen Corp.), or the like. The transfection of the sixth polynucleotide into the mammalian cells having a gene amplification ability may be carried out by transfecting one gene structure including the sixth polynucleotide and the first polynucleotide, or by transfecting the sixth polynucleotide and the first polynucleotide as different gene structures. As to the form and transfecting method of the gene structure into the mammalian cells, the sixth polynucleotides can be described in the same way as the first and second polynucleotides are described.

The present invention includes transfecting the seventh polynucleotide into the mammalian cells simultaneously in transfecting the first and sixth polynucleotides into the mammalian cells, the seventh polynucleotide encoding a transcription activation factor of the promoter. This step improves the activity of the promoter that controls the expression of the target protein, thereby allowing the expression of the target protein that has been under the expression repression caused by the repeated sequence. The seventh polynucleotide is a polynucleotide that encodes the transcription activation factor of the promoter included in the sixth polynucleotide. For example, if the promoter was a TRE promoter, the seventh polynucleotide might be Tet-ON gene (Clontech Laboratories Inc.).

In transfecting the seventh polynucleotide into the mammalian cells and expressing the transcription activation factor, the transfection of the seventh polynucleotide may be carried out by one gene structure into the mammalian cells, the gene structure constructed by controllably linking the seventh polynucleotide with the promoter that promotes the expression of the seventh polynucleotide. The promoter for promoting the expression of the seventh polynucleotide is not particularly limited, provided that the promoter can function in mammalian cells. The promoter may be inducible or non-inducible. Moreover, timing of the transfecting the gene structure including the seventh polynucleotide into the mammalian cells is concurrent with the transfecting the first and sixth polynucleotides (cotransfection). In one simple method, a mixture of (a) the gene structure including the first and sixth polynucleotides and (b) the gene structure including the seventh polynucleotide may be used to transfect the polynucleotides into the mammalian cells by lipofection or the like. As an alternative, a mixture of (i) a gene structure including the first polynucleotide, (ii) a gene structure including the sixth polynucleotide, and (iii) a gene structure including the seventh polynucleotide may be used to transfect the polynucleotides into the mammalian cells by lipofection or the like. As to the form and transfecting method of the gene structure into the mammalian cells, the polynucleotides can be described in the same way as the first and second polynucleotides are described.

The later-described Example 8 discusses how effective the method according to the present embodiment is. In Example 8, it was confirmed that transcription repression of polynucleotides encoding proteins to be expressed was released whereby the expression of the target protein was increased.

The present invention covers a transformant obtained by the method according to the present embodiment.

The steps described in Embodiments 1 to 7 may be appropriately combined. Such combinations of these steps are more effective in releasing the transcription repression caused by the repeated sequence, whereby the expression of the protein having been under the expression repression can be further increased.

Embodiment 8

The present invention encompasses a kit for expressing a protein having been under expression repression, from a repeated sequence formed in mammalian cells in which gene amplification is induced, the kit comprising any ones of the polynucleotides described in Embodiments 1 to 7, an agent, and/or the like in appropriate combinations. The kit according to the present invention makes it possible to easily express a protein having been under expression repression, from a repeated sequence formed in mammalian cells in which gene amplification is induced.

There is no particular limitation in the kit according to the present invention. One example of the kit is a kit including the first polynucleotide and at least one of the third and fourth polynucleotides, where the first polynucleotide includes an origin of replication and a nuclear matrix attachment region that function in eukaryotic cells, the third polynucleotide has a length of 10 kbp or more, and the fourth polynucleotide includes an insulator sequence. The kit may be used according to the method described in Embodiment 1. Moreover, the first and the third and/or fourth polynucleotide may be constituted as one gene structure.

Moreover, one exemplary kit according to the present invention includes the first polynucleotide and the seventh polynucleotide, where the first polynucleotide includes an origin of replication and a nuclear matrix attachment region that function in eukaryotic cells, and the seventh polynucleotide encodes a transcription activation factor of the promoter. After the sixth polynucleotide is prepared by linking the promoter region and target gene, this kit is used according to the method described in Embodiment 3 or 7. The first polynucleotide and the polynucleotide including the promoter region may be constituted as one gene structure.

Another exemplary kit according to the present invention includes the first polynucleotide, a polynucleotide including LoxP gene, and the ninth polynucleotide, where the first polynucleotide includes an origin of replication and a nuclear matrix attachment region that function in eukaryotic cells, and the ninth polynucleotide includes Cre Recombinase gene. After the eighth polynucleotide is prepared by linking, with the target gene, the polynucleotide including the LoxP gene, this kit is used according to the method described in Embodiment 4. The first polynucleotide and the polynucleotide including the LoxP gene may be constituted as one gene structure.

Moreover, the kit according to the present invention may include 5-aza-2'-deoxycytidine, which increases the level of the expression of the protein as described above.

The kit according to the present invention may include an agent, tool, and/or the like necessary for carrying out the method according the present invention described in Embodiments 1 to 7. For example, the kit according to the present invention may include an reagent and a tool necessary for transfecting the polynucleotides into the mammalian cells. Furthermore, the kit may include mammalian cells and a medium or the like for culturing the mammalian cells.

In the following, examples are described referring to the drawing attached herewith, in order to explain the embodiments of the present invention more specifically. Needless to say, the present invention is not limited to these examples and may be modified in various ways in details. Furthermore, the present invention is not limited to the embodiments described above and may be modified within the scope of claims. The technical scope of the present invention also includes embodiments obtained by appropriately combining the disclosed technical means.

Moreover, all the academic documents and patent documents cited in the Description of the present application are incorporated herein by reference.

EXAMPLES

Materials and methods employed in Comparative Examples 1, Reference Example 1, and Examples 1 to 10 are described below.

(Plasmid)

pSFVdhfr (11.0 kbp) was kindly provided from Dr. John Kolman and Dr. Geoffrey M. Wahl (The Salk Institute, San Diego, Calif.). pSFVdhfr has a 4.6 kbp fragment including Ori β derived from 3'-downstream region with respect to hydrofolate reductase (see "Dijkwel, P. A., and Hamlin, J. L. Matrix attachment regions are positioned near replication initiation sites, genes, and an interamplicon junction in the amplified dihydrofolate reductase domain of Chinese hamster ovary cells. Mol. Cell. Biol., 8: 5398-5409, 1988.").

All sequences derived from dihydrofolate reductase is deleted from pSFVdhfr by NotI digestion so as to construct pSFV-V plasmid (6.4 kbp) lacking the origin of replication.

Further, pSFVdhfr(GAP-GFP) was constructed by deleting Hygromycin tolerance gene expressing unit of pSFVdhfr, and embedding, at the position where the expressing unit had been present, a GAP-GFP expressing unit cleaved out from pEPBG plasmid (kindly provided from Dr. Geoffrey M. Wahl, Salk Institute) so that transcription would proceed toward IR.

Moreover, pSFVdhfr/d2EGFP was constructed by deleting Hygromycin tolerance gene-expressing unit of pSFVdhfr, and embedding, at the locus where the expressing unit had been present, a TRE promoter, d2EGFP structuring gene, SV40 poly A sequence (derived from pTRE-d2EGFP (Clontech Laboratories Inc.)) in this order, so that transcription would proceed toward IR.

(Cells)

Human colorectal COLO 320DM and COLO 320HSR tumor cell line (human colon cancer COLO 320DM cell line and human colon cancer COLO 320HSR cell line) were obtained and maintained according to the description in "Shimizu, N., Kanda, T., and Wahl, G. M. Selective capture of acentric fragments by micronuclei provides a rapid method of purifying extrachromosomally amplified DNA. Nat. Genet., 12: 65-71, 1996.".

Moreover, culturing of the cells and transformed cells thereof was carried out according to this document. In short, the cell lines were cultured at 37° C. in the presence of 5% $CO_2$ in a RPMI 1640 medium (Nissui Pharmaceutical Co., Ltd.) to which 10% fetal bovine serum was added.

(Lipofection)

All the plasmids were purified by using Qiagen purification kit (Qiagen Inc., Valencia Calif.), and transfected into cells by Gene Porter 2 lipofection kit (Gene Therapy Systems, San Diego, Calif.).

(Analysis by Cell Sorter)

Fluorescence intensity of these cells were measured by using a cell sorter. The measurement was carried out by sorting 20,000 cells by setting living cells at a gate. The cell sorter used was made by Becton Dickinson, and operated under conditions as described in the manual attached thereto.

Comparative Example 1

Gene Amplification using Plasmid having IR and MAR, and Measurement of Transcription Amount of mRNA (Method)

Into human colon cancer COLO 320 DM cell line, a plasmid (pSFVdhfr) having IR and MAR derived from human DHFR (dihydrofolate reductase) gene was transfected by lipofection. Moreover, as a control, a vector plasmid (pSFV) not having IR and MAR derived from human DHFR (dihydrofolate reductase) gene was transfected into human colon cancer COLO 320 DM cell line by lipofection.

Both the plasmids had a Blasticidin resistance gene. Therefore, transformed cells were selected with 5 µg/ml Blasticidin (Funakoshi Corp.).

(Result)

From the cells transformed with pSFVdhfr, a clone (clone 12) in which gene amplification of the plasmid sequence occurred on double minute (DM), and a clone (clone 22) in which the gene amplification of the plasmid sequence occurred on Homogeneously staining region (HSR) were obtained. Moreover, the cells transformed with the vector plasmid pSFV-V did not increase the gene copy number because of the lack of IR and MAR, but gave transfected cells in which many copies were transfected.

These cells were quantitatively analyzed by Competitive PCR in terms of an amount of DNA of the Blasticidin resistance gene, and an amount of transcribed mRNA. The results are shown in Table 1.

TABLE 1

|  | Gene Copy Number | Level of Expression of RNA (relative ratio) |
| --- | --- | --- |
| pSFV-V | 12 | 1 |
| pSFVdhfr clone 12 | 653 | 3.3 |
| pSFVdhfr clone 22 | 3273 | 0.87 |

As shown in Table 1, it was found that, due to the plasmid (pSFVdhfr) having the IR and MAR, the increase in the copy number of the Blasticidin resistance gene did not lead to the increase in the transcription of the Blasticidin resistance gene to mRNA. It was deduced that repeated sequence was produced as a result of the mass amplification of the gene region including the target gene and the repeated sequence caused transcription repression.

Reference Example 1

Transcription from Gene Amplification Region Caused in Carcinogenesis Process to mRNA Regarding human colon cancer cell line COLO 320DM cell line (ATCC CCL220), it is known that c-myc cancer gene is amplified in carcinogenesis process in patients and locally present on DM or HSR (see "Alitalo, Kari, Schwab, Manfred, Lin, C. C., Varmus, Harold, Bishop, J. Michael, Homogenously staining chromosomal regions contain amplified copies of an abundantly expressed cellular oncogene (c-myc) in malignant neuroendocrine cells from a human colon carcinoma. Proc Nat'l Acad Sci USA. v80., p 1701-1711"). Thus, c-myc cancer gene was quantitatively analyzed by competitive PCR in terms of its copy number and mRNA transcription amount. The competitive PCR was carried out following a method described in "Shimizu et al., Nature Genetics 1996".

The results are shown in Table 2.

TABLE 2

|  | Gene Copy Number | Level of Expression of RNA (relative ratio) |
| --- | --- | --- |
| WI-38 | 1 | 1 |
| COLO 320 DM | 60 | 65 |
| COLO 320 HSR | 24 | 33 |

As shown in Table 2, mRNA transcription in proportion with the copy number of c-myc cancer gene was detected in human colon cancer cell line COLO 320DM and human colon cancer cell line COLO 320HSR. The control was normal human diploid fibrocyte line WI-38.

The results showed that the transcription from the gene amplified gene caused in carcinogenesis process to mRNA was not repressed.

A repeated sequence caused in carcinogenesis process is different from the repeated sequence produced using the plasmid (pSFVdhfr) having IR and MAR in that the repeated sequence caused in carcinogenesis process is long (usually, 100 to 200 kbp) and it is complicated by recombination etc. The results of Comparative Example 1 and Reference Example 1 suggested that a longer repeating unit and more complicated repeating structure would increase the mRNA transcription amount from the repeated sequence produced using the plasmid having IR and MAR.

Example 1

Effect of Transfecting λ-Phage DNA and Target Gene into Host Cells

A plasmid (pSFVdhfr (GAP-GFP)) and λ-phage DNA were mixed at a ratio of 1:2 by weight. The plasmid had IR and MAR derived from human DHFR (dihydrofolate reductase) locus, and expresses a fused protein from GFP (Green Fluorescence Protein) gene and GAP (G-associated polypeptide) gene. The mixture of the plasmid and λ-phage DNA was transfected to human colon cancer cells COLO 320DM cells by lipofection. From 2 days from the gene transfection, the cells were selected using 5 µg/ml of Blasticidin (Funakoshi Corp.) that was selective to Blasticidin tolerance gene on the plasmid. After 3 to 4 weeks, many colonies of transformed cells were obtained.

Figure 1:
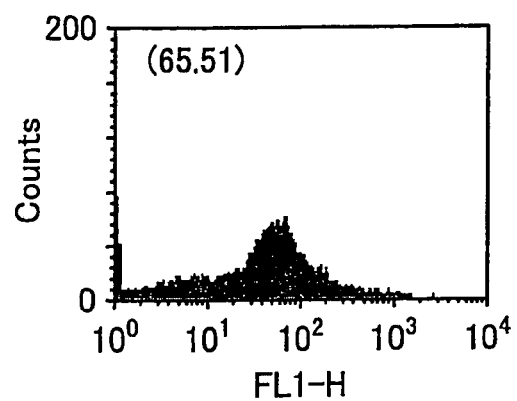
FIG. 1(a) is a view illustrating a fluorescence intensity of a control of Example 1, where only pSFVdhfr (GAP-GFP), but not λ-phage DNA, was transfected into cells.
FIG. 1(b) is a view illustrating a fluorescence intensity of a case of Example 1, where a mixture of pSFVdhfr (GAP-GFP) and λ-phage DNA was transfected into cells (cotransfection).
Figure 1:
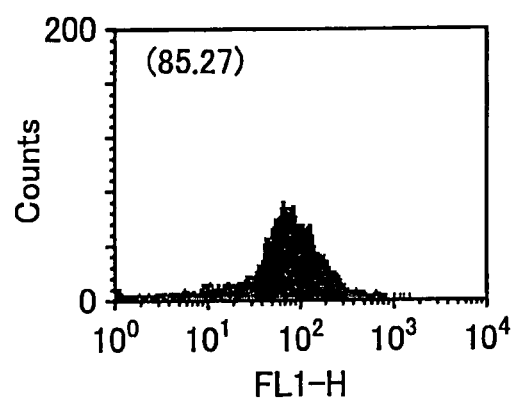

FIG. 1 shows results of fluorescence intensity analysis of GFP by using a cell sorter. FIG. 1(a) shows the result of a case where only pSFVdhfr (GAP-GFP), but not λ-phage DNA, was transfected into the cells. FIG. 1(b) shows a result of a case where pSFVdhfr (GAP-GFP) and λ-phage DNA was transfected into the cells (cotransfection). In parenthesis in FIG. 1, averages of fluorescence intensity is shown.

Fluorescence intensity in the case where the mixture of pSFVdhfr (GAP-GFP) and λ-phage DNA was transfected into the cells (cotransfection) was 85.27, while the control had a fluorescence intensity of 65.51. Thus, this indicated that cotransfection clearly increases expression of GFP (target protein). In other words, it was found that coamplification of (a) a polynucleotide encoding a target protein and (b) λ-phage DNA releases the repeated sequence-caused expression repression on the protein.

Example 2

Effect of Transfection of Insulator Sequence and Target Gene into Host Cells (Method)

A plasmid DNA having HS4 insulator sequence derived from Aves (see "Recillas-Targa, F. et al., Proc. Natl. Acad. Sci. U.S.A., vol. 99, p 6883-6888, (2002)") and a plasmid (pSFVdhfr/d2EGFP) were mixed and transfected into human colon cancer cell COLO 320DM cells by lipofection. The plasmid (pSFVdhfr/d2EGFP) was a plasmid having (a) IR and MAR derived from human DHFR gene locus, (b) Blasticidin tolerance gene, and (c) d2EGFP gene that was under control of TRE-promoter (Tetracycline inducing promoter). The plasmid DNA having the Aves-derived HS4 insulator sequence was a plasmid having 5' HS4 insulator sequence of 1.2 kbp described in the paper of Recillas-Targa, F. et al. From 2 days from the gene transfection, the cells were selected using 5 µg/ml of Blasticidin (Funakoshi Corp.) that was selective to Blasticidin tolerance gene on the plasmid. After 3 to 4 weeks, many colonies of transformed cells were obtained.

From 2 days from the gene transfection, the cells were selected using 5 µg/ml of Blasticidin (Funakoshi Corp.) that was selective to Blasticidin tolerance gene on the plasmid. After 3 to 4 weeks, many colonies of transformed cells were obtained. After that, the transformed cells were selected by passaging in media of increasing concentration of Blasticidin (up to final concentration of 320 µg/ml) with passage intervals of 3 to 6 days.

(Results)

Figure 2:
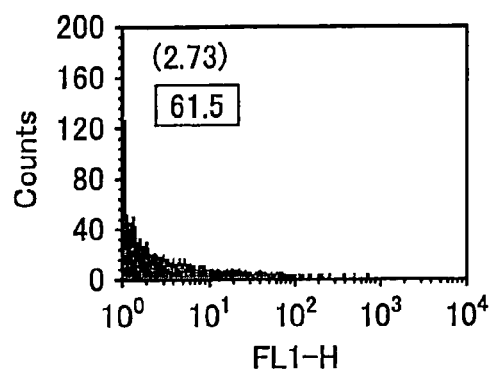
FIG. 2(a) is a view illustrating a fluorescence intensity of a control of Example 2, where only pSFVdhfr/d2EGFP was transfected into cells.
FIG. 2(b) is a view illustrating a fluorescence intensity of a case of Example 2, where only pSFVdhfr/d2EGFP was transfected into cells, and the cells were selected with 80 µg/ml of Blasticidin.
FIG. 2(c) is a view illustrating a fluorescence intensity of a case of Example 2, where a mixture of pSFVdhfr/d2EGFP and a plasmid DNA having an Aves-derived HS4 insulator sequence was transfected into cells.
FIG. 2(d) is a view illustrating a fluorescence intensity of a case of Example 2, where a mixture of pSFVdhfr/d2EGFP and a plasmid DNA having the Aves-derived HS4 insulator sequence was transfected into cells, and the cells were selected with 80 µg/ml of Blasticidin.
Figure 2:
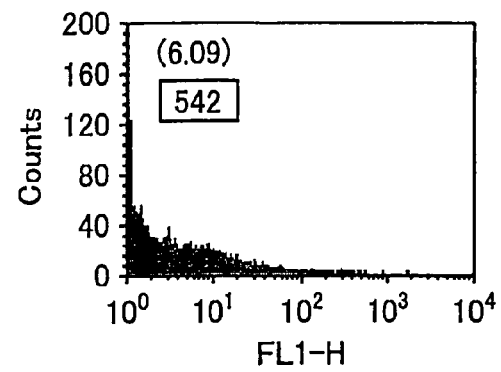
Figure 2:
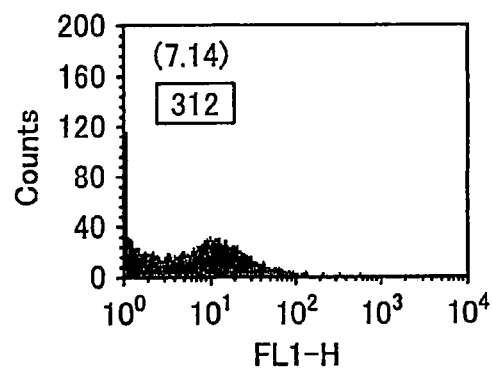
Figure 2:
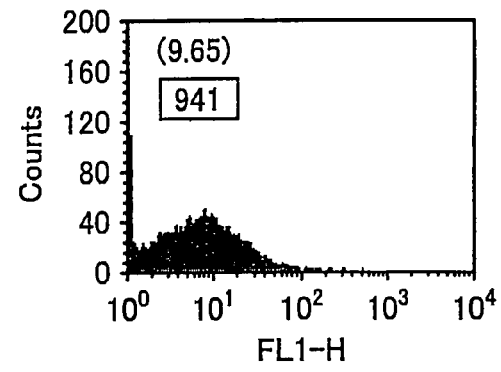

FIG. 2 shows results of fluorescence intensity analysis of GFP by using a cell sorter.

FIG. 2(a) shows a result of control where only pSFVdhfr/d2EGFP was transfected into cells. FIG. 2(b) shows a result of a case where only pSFVdhfr/d2EGFP was transfected into cells and the cells were then selected with 80 µg/ml of Blasticidin. FIG. 2(c) shows a result of a case where pSFVdhfr/d2EGFP and the plasmid DNA having the Aves-derived HS4 insulator sequence were mixed and transfected into the cells. FIG. 2(d) shows a result of a case where pSFVdhfr/d2EGFP and the plasmid DNA having the Aves-derived HS4 insulator sequence were mixed and transfected into the cells, and the cells were then selected with 80 µg/ml of Blasticidin. In parenthesis in FIG. 2, averages of fluorescence intensity is shown.

In this method for detecting the fluorescence intensity, detection limit was 1, and all fluorescence intensities of 1 or less would be detected as 1. In view of this, a product of a ratio (cell %) of cells of fluorescence intensities of 2 or more in all living cells (10,000 cells) and an average of the fluorescence intensities of the cells having fluorescence intensities of 2 or more was calculated out for each experimental plot. This product is referred to as "accumulated fluorescence intensity" hereinafter and in later Examples and shown in boxed letter in the figures.

While the control shown in FIG. 2(a) had an average fluorescence intensity of 2.73 and an accumulated fluorescence intensity of 61.5, the case shown in FIG. 2(c) where pSFVdhfr/d2EGFP and the plasmid DNA having the Aves-derived HS4 insulator sequence were mixed and transfected into the cells had an average fluorescence intensity of 7.14 and an accumulated fluorescence intensity of 312. This clearly demonstrated that the expression of d2EGFP, which was the target protein, was increased as a result of the cotransfection subsequent coamplification of the target protein-encoding gene and the Aves-derived HS4 insulator sequence.

Moreover, the average fluorescence intensity was 6.09 and the accumulated fluorescence intensity was 542 in the case shown in FIG. 2(b) where only pSFVdhfr/d2EGFP was transfected into cells and the cells were then selected with 80 µg/ml of Blasticidin, while the control shown in FIG. 2(a) had the average fluorescence intensity of 2.73 and the accumulated fluorescence intensity of 61.5. the average fluorescence intensity was 9.65 and the accumulated fluorescence intensity was 941 in the case shown in FIG. 2(d) where a result of a case where pSFVdhfr/d2EGFP and the plasmid DNA having the Aves-derived HS4 insulator sequence were mixed and transfected into the cells, and the cells were then selected with 80 µg/ml of Blasticidin, while the case shown in FIG. 2(c) where pSFVdhfr/d2EGFP and the plasmid DNA having the Aves-derived HS4 insulator sequence were mixed and transfected into the cells had an average fluorescence intensity of 7.14 and an accumulated fluorescence intensity of 312.

This demonstrated that the expression of the target protein could be increased by selecting, with Blasticidin of stepwise increasing concentrations, the cells in which the gene amplification occurred. Moreover, this showed that the expression of the target protein, d2EGFP, was further increased by performing cotransfection and subsequent coamplification of the target protein-encoding gene and the Aves-derived HS4 insulator sequence, and then selecting the cells with Blasticidin of stepwise increasing concentrations. In other words, the combination of means for increasing expression of the target proteins makes it possible to attain further higher expression of the target protein.

Example 3

Effect of Selecting Transformed Cells with Selective Chemical of Stepwise Increasing Concentrations (Method)

A plasmid (pSFVdhfr/d2EGFP) was transfected into human colon cancer cell COLO 320DM cells by lipofection. The plasmid (pSFVdhfr/d2EGFP) was a plasmid having (a) IR and MAR derived from human DHFR gene locus, (b) Blasticidin tolerance gene, and (c) d2EGFP gene that was under control of TRE-promoter (Tetracycline inducing promoter). The transformed cells were selected with 5 μg/ml of Blasticidin (Funakoshi Corp.) thereby obtaining many transformed clones. After the clones were mixed, the culturing was continued. Passaging was carried out subsequently with media having Blasticidin concentrations doubled (from 5 μg/ml to 320 μg/ml) every passage intervals of 3 to 5 days. Cells select with the respective Blasticidin concentrations were treated with 1 μg/ml of Doxycycline (Clontech Laboratories Inc.) added to the media so as to activate TRE-promoter and thereby inducing expression of d2EGFP (whose half-life is much shorter than general EGFP.

(Result)

Figure 3:
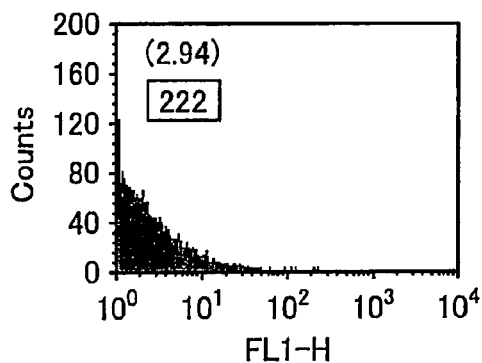
FIG. 3(a) is a view illustrating a fluorescence intensity of cells selected with 5 µg/ml of Blasticidin in Example 3.
FIG. 3(b) is a view illustrating a fluorescence intensity of cells selected with 10 µg/ml of Blasticidin in Example 3.
FIG. 3(c) is a view illustrating a fluorescence intensity of cells selected with 40 µg/ml of Blasticidin in Example 3.
FIG. 3(d) is a view illustrating a fluorescence intensity of cells selected with 160 µg/ml of Blasticidin in Example 3.
FIG. 3(e) is a view illustrating a fluorescence intensity of cells selected with 320 µg/ml of Blasticidin in Example 3.
Figure 3:
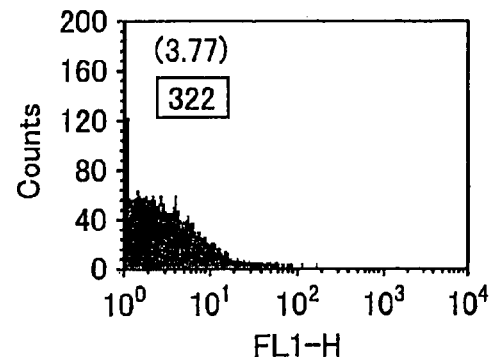
Figure 3:
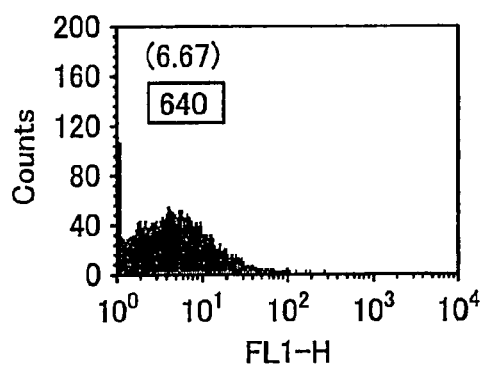
Figure 3:
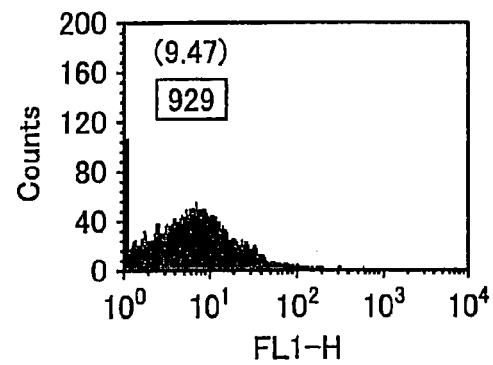
Figure 3:
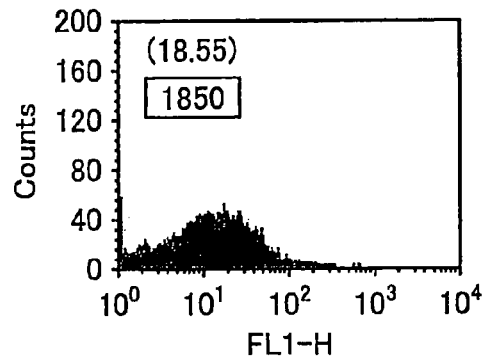

FIG. 3 shows a result of analysis on the level of the expression of d2EGFP in the cells of each case using cell sorter.

FIG. 3(a) shows a result of the cells selected with 5 μg/ml of Blasticidin. FIG. 3(b) shows a result of the cells selected with 10 ng/ml of Blasticidin. FIG. 3(c) shows a result of the cells selected with 40 μg/ml of Blasticidin. FIG. 3(d) shows a result of the cells selected with 160 μg/ml of Blasticidin. FIG. 3(e) shows a result of the cells selected with 320 μg/ml of Blasticidin. In FIG. 3, the value in parenthesis is an average of fluorescence intensities (i.e., average fluorescence intensity), and boxed value is an accumulated fluorescence intensity.

As shown in FIG. 3(a), the cells select with 5 μg/ml of Blasticidin had an average fluorescence intensity of 2.94 and an accumulated fluorescence intensity of 222. As shown in FIG. 3(b), the cells select with 10 ng/ml of Blasticidin had an average fluorescence intensity of 3.77 and an accumulated fluorescence intensity of 322. As shown in FIG. 3(c), the cells select with 40 μg/ml of Blasticidin had an average fluorescence intensity of 6.67 and an accumulated fluorescence intensity of 640. As shown in FIG. 3(d), the cells select with 160 μg/ml of Blasticidin had an average fluorescence intensity of 9.47 and an accumulated fluorescence intensity of 929. As shown in FIG. 3(e), the cells select with 320 μg/ml of Blasticidin had an average fluorescence intensity of 18.55 and an accumulated fluorescence intensity of 1850.

This demonstrated that the selecting the transformed cells with the stepwise increasing chemical concentrations can increase the expression of the target protein.

Example 4

Effect of Promoter for Controlling Expression of Target Protein

By lipofection, pTet-ON plasmid (Clontech Laboratories Inc.) having Tet-ON gene encoding a transcription activation factor (Tet-ON protein) for activating TRE-promoter was transfected into human cancer COLO 320DM cells. Then, stable transformed cells were selected with hygromycin. Into the cells thus obtained (hereinafter referred to as "Tet-ON cells"), a mixture of a plasmid (pSFVdhfr/d2EGFPI) and the plasmid having the Aves-derived HS4 insulator sequence was transfected by lipofection. The plasmid (pSFVdhfr/d2EGFP) was a plasmid having (a) IR and MAR derived from human DHFR gene locus, (b) Blasticidin tolerance gene, and (c) d2EGFP gene that was under control of TRE-promoter (Tetracycline inducing promoter). Then, stable transformant was selected with Blasticidin. The plasmid having the Aves-derived HS4 insulator sequence was identical with the one described in Example 2.

Next, by lipofection the pTet-ON plasmid was introduced again into the cells thus obtained. Two days later when transient expression occurred, a level of the expression of d2EGFP was measured.

In general, Tet-ON protein (rtTA) is expressed at a low expression level in the stable transformed cells, while the expression is high level of expression in the transient expression. Therefore, the level of the expression of d2EGFP in the stable transformed cells was regarded as a result of normal expression of Tet-ON protein, while the level of the expression of d2EGFP in the case of the transient expression was regarded as a result of high expression of Tet-ON protein.

(Result)

Figure 4:
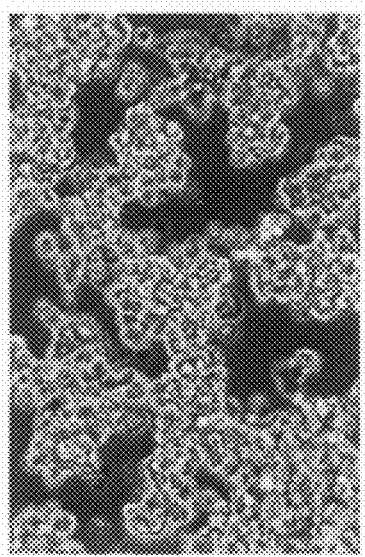
FIG. 4(a) is a phase contrast microscopic image (×200) of cells in which normal expression of Tet-ON gene occurred in Example 4.
FIG. 4(b) is a phase contrast microscopic image (×200) of cells in which high expression of Tet-ON gene occurred in Example 4.
FIG. 4(c) is a fluorescence microscopic image (×200) of cells in which normal expression of Tet-ON gene occurred in Example 4.
FIG. 4(d) is a fluorescence microscopic image (×200) of cells in which high expression of Tet-ON gene occurred in Example 4.
Figure 4:
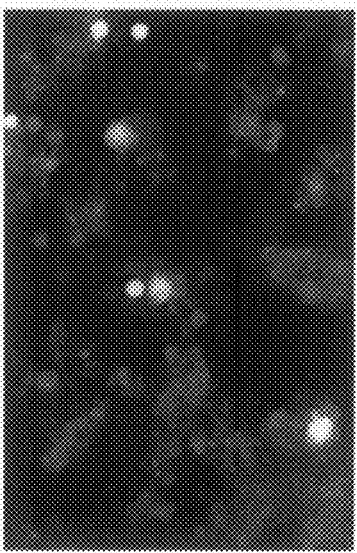
Figure 4:
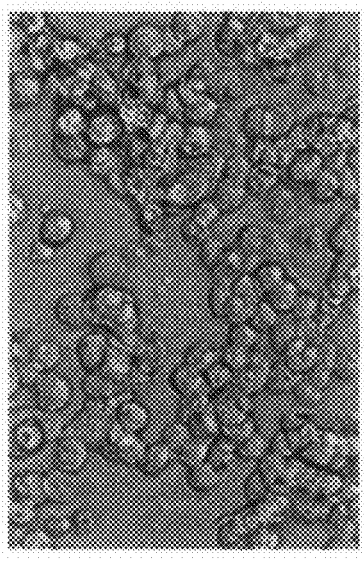
Figure 4:
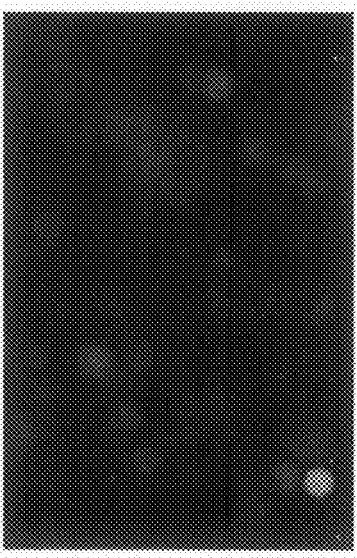

FIG. 4 illustrate phase contrast microscopic images and fluorescent microscopic images of the cells of each case. Moreover, FIG. 5 illustrate results of analysis of the level of the expression of d2EGFP in the cells of each case by using a cell sorter.

FIG. 4(a) is a phase contrast microscopic image (×200) of cells in the normal expression of Tet-ON protein. FIG. 4(b) is a phase contrast microscopic image (×200) of cells in the high expression of Tet-ON protein. FIG. 4(c) is a fluorescent microscopic image (×200) of cells in the normal expression of Tet-ON protein. FIG. 4(d) is a fluorescent microscopic image (×200) of cells in the high expression of Tet-ON protein.

Figure 5:
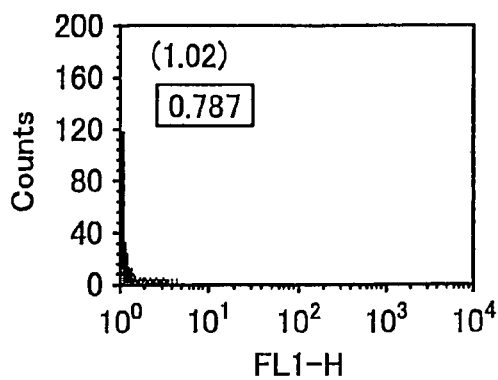
FIG. 5(a) is a view illustrating a fluorescence intensity of cells in which pSFVdhfr/d2EGFP was transfected and normal expression of Tet-ON protein occurred in Example 4.
FIG. 5(b) is a view illustrating a fluorescence intensity of cells in which pSFVdhfr/d2EGFP was transfected and high expression of Tet-ON protein occurred in Example 4.
FIG. 5(c) is a view illustrating a fluorescence intensity of cells in which the Aves-derived HS4 insulator sequence and pSFVdhfr/d2EGFP were coamplified and normal expression of Tet-ON protein occurred in Example 4.
FIG. 5(d) is a view illustrating a fluorescence intensity of cells in which the Aves-derived HS4 insulator sequence and pSFVdhfr/d2EGFP were coamplified and high expression of Tet-ON protein occurred in Example 4.
Figure 5:
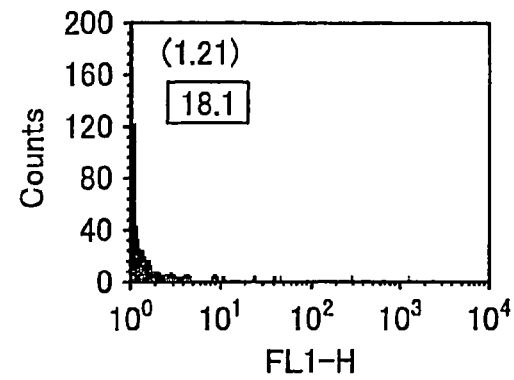
Figure 5:
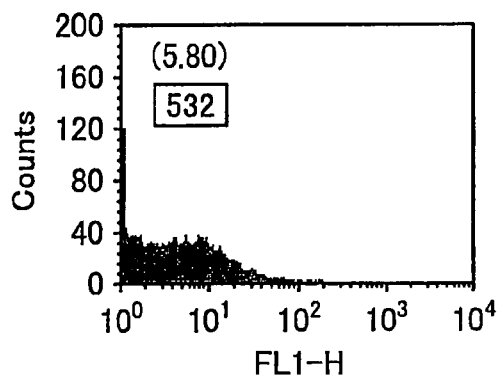
Figure 5:
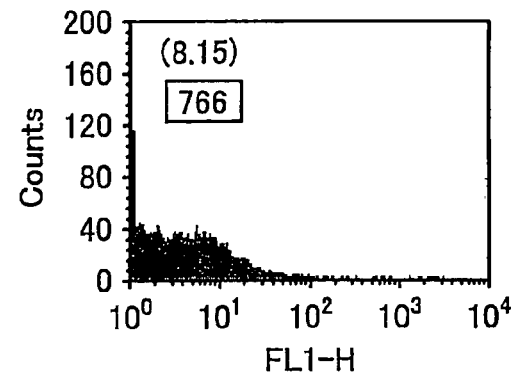

Moreover, FIG. 5(a) illustrates fluorescence intensity of the normal expression of Tet-ON protein of the cells in which the plasmid prepared by transfecting the d2EGFP gene under control of the TRE-promoter into pSFV-V plasmid not having an origin of replication nor a nuclear matrix attachment region. FIG. 5(b) illustrates fluorescence intensity of the high expression of Tet-ON protein of the cells in which the plasmid prepared by transfecting the d2EGFP gene under control of the TRE-promoter into the pSFV-V plasmid. FIG. 5(c) illustrates fluorescence intensity of the normal expression of Tet-ON protein of the cells in which the Aves-derived HS4 insulator sequence was amplified simultaneously with pSFVdhfr/d2EGFPI. FIG. 5(d) illustrates fluorescence intensity of the high expression of Tet-ON protein of the cells in which the Aves-derived HS4 insulator sequence was amplified simultaneously with pSFVdhfr/d2EGFPI. In FIG. 5, the value in parenthesis is an average of fluorescence intensities (i.e., average fluorescence intensity), and boxed value is an accumulated fluorescence intensity.

From FIGS. 4(a) to 4(d), it was clear that the fluorescence intensity of the cells with the high expression of Tet-ON protein was higher than that of the stable transformed cells with the normal expression of Tet-ON protein (especially, see FIGS. 4(c) and 4(d)).

Moreover, the average fluorescence intensity was 1.02 and the accumulated fluorescence intensity was 0.787 in FIG. 5(a), while the average fluorescence intensity was 1.21 and the accumulated fluorescence intensity was 18.1 in FIG. 5(b). Further, the average fluorescence intensity was 5.80 and the accumulated fluorescence intensity was 532 in FIG. 5(c), while the average fluorescence intensity was 8.15 and the accumulated fluorescence intensity was 766 in FIG. 5(d). This indicates that the fluorescence intensity increased, that is, the level of the expression of the target protein increased in the case of high expression of Tet-ON protein regardless of the copy number of the gene amplification. Further, the fluorescence intensity (FIG. 5(d)) of the cells in which the Aves-derived HS4 insulator sequence was amplified simultaneously with pSFVdhfr/d2EGFPI and the high expression of Tet-ON protein occurred (FIG. 5(d); the average fluorescence intensity was 8.15 and the accumulated fluorescence intensity was 766). This showed that the expression of a target protein can be further increased by combining means for increasing expression of the protein.

Example 5

Effect of Extrachromosomally Cleaving Out Gene Encoding Target Protein in Amplification Region (Method)

A plasmid was constructed by removing Hygromycin tolerance gene from the pSFVdhfr/d2EGFP plasmid and embedding synthetic loxP sequence (46 bp) in the downstream of Blasticidin resistance gene. The synthetic loxP sequence (46 bp) was prepared by synthesizing a DNA fragment having the base sequence of 5'-GCGCGGCCGCAT-AACTTCGTATAGCATACATTATACGAAGTTATGCG GCCGCGC-3' (SEQ. ID. NO. 1), by using a well-known DNA synthesizer. Note that GCGGCCGC on both the terminals (5' terminal and 3' terminal) of the loxP sequence was Not I identifying sequence for cloning.

The plasmid thus prepared was transfected into human colon cancer cells COLO 320DM cells by lipofection. The cells thus transformed were selected with 5 μg/ml of Blasticidin. The transformed cells thus prepared was transformed with a plasmid having Cre Recombinase gene (kindly provided from Dr. Rolf Springer (Max-Planck-Institut, Germany). see "Shimshek, D. R., J. Kim, M. R. Hubner, D. J. Spergel, F. Buchholz, E. Casanova, A. F. Stewart, P. H. Seeburg, and R. Springer. 2002. Codon-improved Cre recombinase (iCre) expression in the mouse. Genesis. 32:19-26") and then cultured for 1 week.

(Result)

Figure 6:
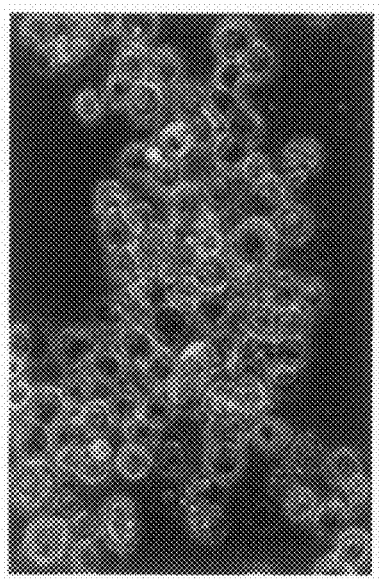
FIG. 6(a) is a phase contrast microscopic image (×200) of cells before transfection of Cre Recombinase gene in Example 5.
FIG. 6(b) is a phase contrast microscopic image (×200) of cells after the transfection of the Cre Recombinase gene in Example 5.
FIG. 6(c) is a fluorescence microscopic image (×200) of cells before the transfection of the Cre Recombinase gene in Example 5.
FIG. 6(d) is a fluorescence microscopic image (×200) of cells after the transfection of the Cre Recombinase gene in Example 5.
Figure 6:
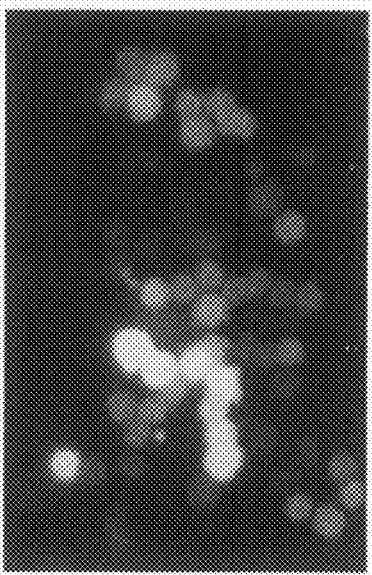
Figure 6:
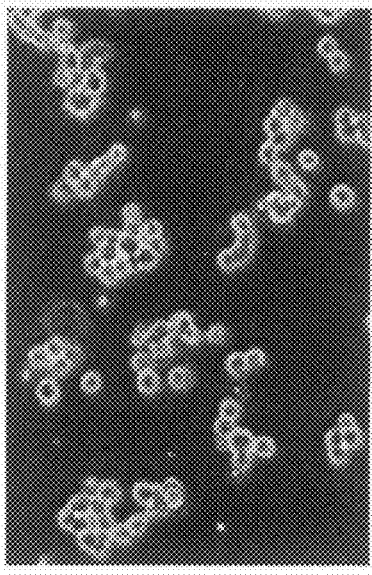
Figure 6:
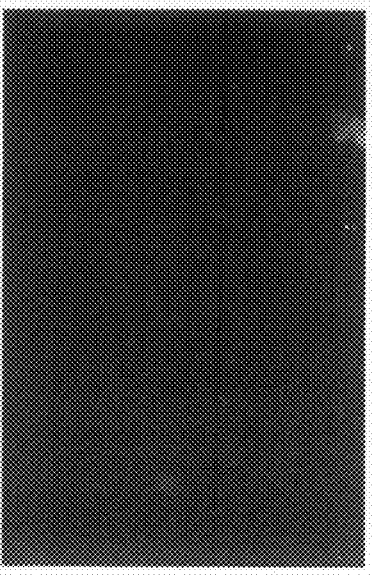

FIG. 6 illustrates phase contrast microscopic images and fluorescence microscopic images of the cells of each case. FIG. 6(a) is a phase contrast microscopic image (×200) of the cells before the transfection of the Cre Recombinase gene. FIG. 6(b) is a phase contrast microscopic image (×200) of cells after the transfection of the Cre Recombinase gene. FIG. 6(c) is a fluorescent microscopic image (×200) of cells before the transfection of the Cre Recombinase gene. FIG. 6(d) is a fluorescent microscopic image (×200) of cells after the transfection of the Cre Recombinase gene.

In FIGS. 6(a) to 6(d) it was clearly showed that the fluorescence intensity of the cells after the transfection of the Cre Recombinase gene was higher than before the transfection (see especially, FIGS. 6(c) and 6(d)). Therefore, it was demonstrated that the extrachromosomal cleavage of the gene region causing the repeated sequence by the gene amplification makes it possible to express the target protein that has been under expression repression.

Example 6

Treatment of Cells with 5-aza-2'-deoxycytidine (Method)

A mixture of a plasmid (pSFVdhfr/d2EGFP) and the plasmid DNA having the Aves-derived HS4 insulator sequence was transfected to human colon cancer cells COLO 320DM cells by lipofection. The plasmid (pSFVdhfr/d2EGFP) was a plasmid having (a) IR and MAR derived from human DHFR gene locus, (b) Blasticidin tolerance gene, and (c) d2EGFP gene that was under control of TRE-promoter (Tetracycline inducing promoter). The plasmid DNA having the Aves-derived HS4 insulator sequence was identical with the one described in Example 2. From 2 days later since the gene transfection, the cells were selected with 5 μg/ml of Blasticidin (Funakoshi Corp.). After 3 to 4 weeks, many colonies of transformed cells were obtained.

Into a culture solution of the transformed cells, of 1 μM or 3 μM of 5-aza-2' deoxycytidine (hereinafter referred to as "5-aza" where appropriate; Sigma) was added. Thereby, the cells were treated with 5-aza for 3 days. For comparison purposes, 20 nM of Trichostatin A (hereinafter referred to as "TSA" where appropriate; histone deacetylation inhibitor, Sigma), which is known as a material for increasing gene expression from the repeated sequence, was added to some culture solutions of the transformed cells and analyzed.

(Result)

Figure 7:
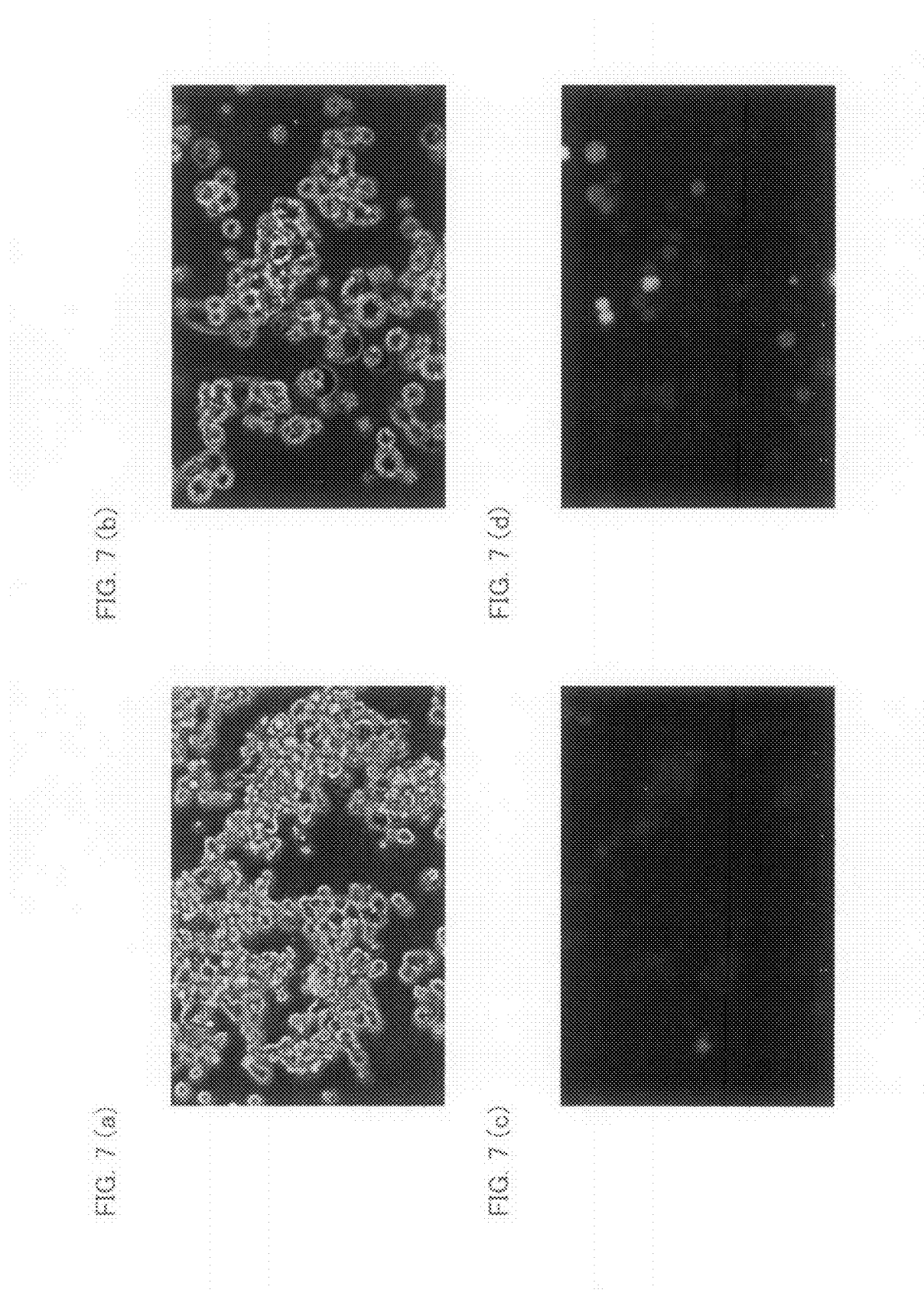
FIG. 7(a) is a phase contrast microscopic image (×200) of cells before treatment with 5-aza-2'-deoxycytidine (5-aza) in Example 6.
FIG. 7(b) is a phase contrast microscopic image (×200) of cells after treatment with 1 μM of 5-aza in Example 6.
FIG. 7(c) is a fluorescence microscopic image (×200) of cells before treatment with 5-aza in Example 6.
FIG. 7(d) is a fluorescence microscopic image (×200) of cells after treatment with 1 μM of 5-aza in Example 6.
Figure 8:
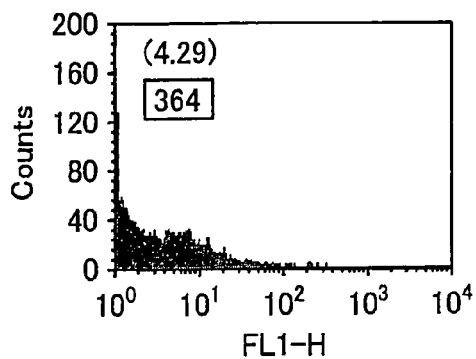
FIG. 8(a) is a view illustrating a fluorescence intensity of cells before treatment with 5-aza-2'-deoxycytidine (5-aza) in Example 6.
FIG. 8(b) is a view illustrating a fluorescence intensity of cells after treatment with 20 nM of Trichostatin A (TSA) in Example 6.
FIG. 8(c) is a view illustrating a fluorescence intensity of cells after treatment with 1 μM of 5-aza in Example 6.
FIG. 8(d) is a view illustrating a fluorescence intensity of cells after treatment with 1 μM of 5-aza and 20 nM of TSA in Example 6.
FIG. 8(e) is a view illustrating a fluorescence intensity of cells after treatment with 3 μM of 5-aza in Example 6.
FIG. 8(f) is a view illustrating a fluorescence intensity of cells after treatment with 3 μM of 5-aza and 20 nM of TSA in Example 6.
Figure 8:
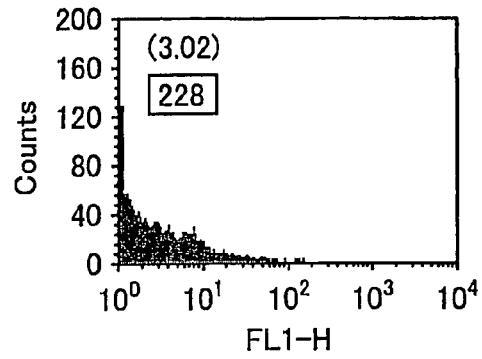
Figure 8:
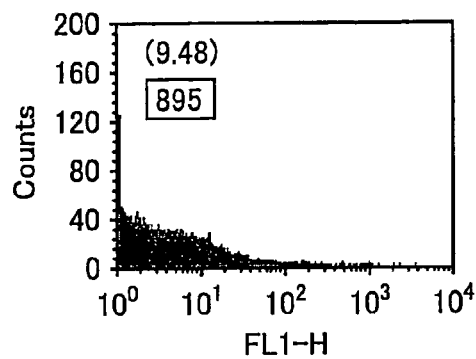
Figure 8:
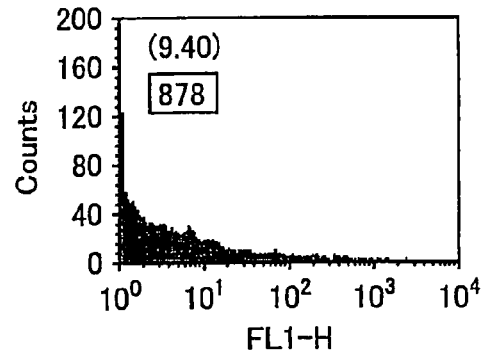
Figure 8:
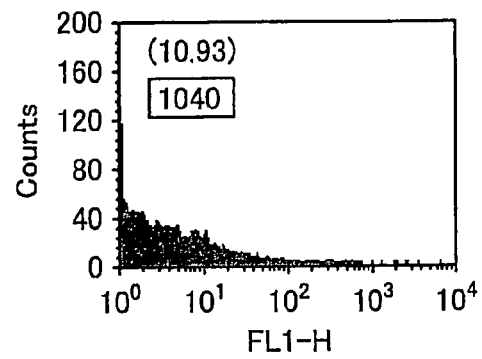
Figure 8:
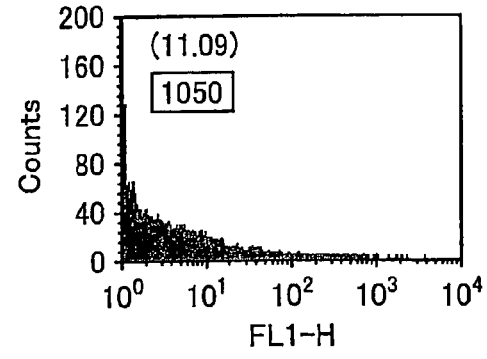

FIG. 7 illustrate phase contrast microscopic images and fluorescence microscopic images of the cases of each case. FIG. 8 illustrate results of analysis of the level of the expression of d2EGFP in the cells of each case by using a cell sorter.

FIG. 7(a) illustrates a phase contrast microscopic image (×200) of the cells before the treatment with 5-aza. FIG. 7(b) illustrates a phase contrast microscopic image (×200) of the cells after the treatment with 5-aza. FIG. 7(c) illustrates a fluorescence microscopic image (×200) of the cells before the treatment with 5-aza. FIG. 7(d) illustrates a fluorescence microscopic image (×200) of the cells after the treatment with 5-aza.

Furthermore, FIG. 8(a) illustrates the fluorescence intensity of the cells before the 5-aza treatment. FIG. 8(b) illustrates the fluorescence intensity of the cells after the treatment with 20 nM of TSA. FIG. 8(c) illustrates the fluorescence intensity of the cells after the treatment with 1 μM of 5-aza. FIG. 8(d) illustrates the fluorescence intensity of the cells after the treatment with 1 μM of 5-aza and 20 nM of TSA. FIG. 8(e) illustrates the fluorescence intensity of the cells after the treatment with 3 μM of 5-aza. FIG. 8(f) illustrates the fluorescence intensity of the cells after the treatment with 3 μM of 5-aza and 20 nM of TSA. In FIG. 8, the value in parenthesis is an average of fluorescence intensities (i.e., average fluorescence intensity), and boxed value is an accumulated fluorescence intensity.

In FIGS. 7(a) to 7(d), it was clearly demonstrated that the fluorescence intensity of the cells after the treatment with 5-aza was higher than that of the cells before the treatment with 5-aza (especially, see FIGS. 7(c) and 7(d)).

Moreover, the average fluorescence intensity was 4.29 and the accumulated fluorescence intensity was 364 in the cells before the treatment with 5-aza illustrated in FIG. 8(a), while the average fluorescence intensity was 9.48 and the accumulated fluorescence intensity was 895 in the cells after the treatment with 1 µM of 5-aza illustrated in FIG. 8(c). This showed that the expression of d2EGFP, which was the target protein, was increased by treating the cells with 5-aza. As illustrated in FIG. 8(e), the cells after the treatment with 3 µM of 5-aza showed the average fluorescence intensity of 10.93 and the accumulated fluorescence intensity of 1040 which were higher than in the cells after the treatment with 1 µM of 5-aza. This demonstrated that the treatment with 5-aza of higher concentration further increases the expression of the target protein.

On the other hand, the average fluorescence intensity was 3.02 and the accumulated fluorescence intensity was 228 in the cells after the treatment with 20 nM of TSA illustrated in FIG. 8(b), while the average fluorescence intensity was 4.29 and the accumulated fluorescence intensity was 364 in the cells before the treatment with 5-aza illustrated in FIG. 8(a). This showed that the treatment with 20 nM of TSA cannot increase the expression of the target protein. Moreover, the average fluorescence intensity was 9.40 and the accumulated fluorescence intensity was 878 in the cells after the treatment with 1 µM of 5-aza and 20 nM of TSA illustrated in FIG. 8(d), while the average fluorescence intensity was 9.48 and the accumulated fluorescence intensity was 895 in the cells after the treatment with 1 µM of 5-aza illustrated in FIG. 8(c). Further, the average fluorescence intensity was 11.09 and the accumulated fluorescence intensity was 1050 in the cells after the treatment with 3 µM of 5-aza and 20 nM of TSA illustrated in FIG. 8(f), while the cells after the treatment with 3 µM of 5-aza showed the average fluorescence intensity of 10.93 and the accumulated fluorescence intensity of 1040 illustrated in FIG. 8(e). This explained that the combination of 5-aza and TSA cannot increase the expression of the target protein.

Example 7

Effect of Selecting Clone in which Gene Amplification Occurred on DM (Method)

By lipofection, the pTet-ON plasmid (Clontech Laboratories Inc.) having Tet-ON gene encoding a transcription activating factor (Tet-ON protein) for promoting TRE-promoter was transfected into human colon cancer COLO 320DM. Transformed cells (hereinafter referred to as "Tet-ON cells") which stably expressed Tet-ON protein, were selected with Hygromycin.

Next, the pSFVdhfr/d2EGFP plasmid was transfected into the Tet-ON cells by lipofection. The cells thus obtained were selected with 5 µg/ml of Blasticidin for approximately 3 weeks, thereby obtaining a polyclonal population of the stable transformed cells.

Figure 9:
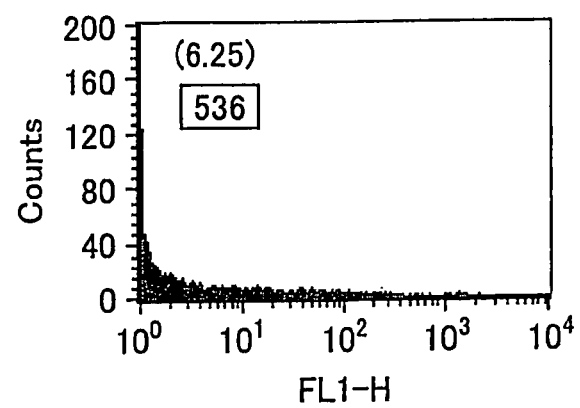
FIG. 9 is a view illustrating the result of analysis of a level of expression of d2EGFP in a polyclonal population of Tet-ON cells by using a cell sorter, where pSFVdhfr/d2EGFP was transfected in the Tet-ON cells and the expression of d2EGFP was induced with Doxycycline in Example 7.

The expression of d2EGFP was induced in the polyclonal population by activating TRE-promoter by adding 5 µg/ml of Doxycycline (Clontech Laboratories Inc.) in the medium. FIG. 9 illustrates a result of analysis of the level of the expression of d2EGFP in this case by using a cell sorter. In FIG. 9, the value in parenthesis is an average of fluorescence intensities (i.e., average fluorescence intensity), and boxed value is an accumulated fluorescence intensity. Based on the result of FIG. 9, it was confirmed that the polyclonal population was a population for expressing d2EGFP (average fluorescence intensity: 6.25, accumulated fluorescence intensity: 536).

From the polyclonal population, given 30 clones were obtained by a limiting dilution method that was carried out by inoculating a clone to 6 well plates with such a low cell concentration of 30 cells/ml, and incubating the plates for 10 days to 2 weeks thereby obtaining colonies thereon.

From among the clones, 4 clones having high levels of expression of d2EGFP (Clone 4, Clone 5, Clone 6, and Clone 9) were selected by fluorescence microscopic observation. Mitotic chromosome samples of the 4 clones were prepared. By FISH method, detection for a base sequence derived from the transfected pSFVdhfr/d2EGFP plasmid was carried out. The preparation of mitotic chromosome samples and the FISH method were carried out as described in Shimizu, N., Kanda, T., and Wahl, G. M. Selective capture of acentric fragments by micronuclei provides a rapid method of purifying extrachromosomally amplified DNA. Nature Genet., 12: 65-71, 1996.

Figure 10:
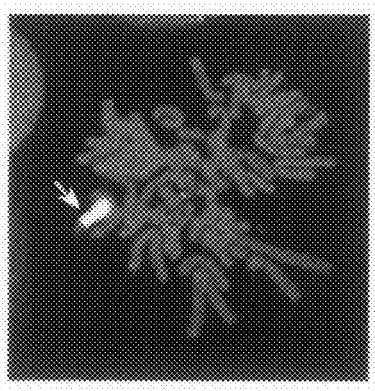
FIG. 10(a) is a fluorescence microscopic image illustrating the result of detection of a base sequence of pSFVdhfr/d2EGFP plasmid in clone 4 by FISH method, where clone 4 was selected from among the polyclonal population of Tet-ON cells in which pSFVdhfr/d2EGFP was transfected in Example 7.
FIG. 10(b) is a fluorescence microscopic image illustrating the result of detection of a base sequence of pSFVdhfr/d2EGFP plasmid in clone 5 by FISH method, where clone 5 was selected from among the polyclonal population of Tet-ON cells in which pSFVdhfr/d2EGFP was transfected in Example 7.
FIG. 10(c) is a fluorescence microscopic image illustrating the result of detection of a base sequence of pSFVdhfr/d2EGFP plasmid in clone 6 by FISH method, where clone 6 was selected from among the polyclonal population of Tet-ON cells in which pSFVdhfr/d2EGFP was transfected in Example 7.
FIG. 10(d) is a fluorescence microscopic image illustrating the result of detection of a base sequence of pSFVdhfr/d2EGFP plasmid in clone 9 by FISH method, where clone 9 was selected from among the polyclonal population of Tet-ON cells in which pSFVdhfr/d2EGFP was transfected in Example 7.
Figure 10:
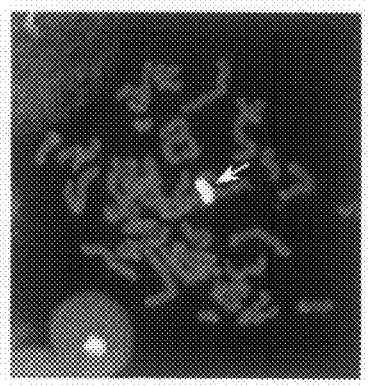
Figure 10:
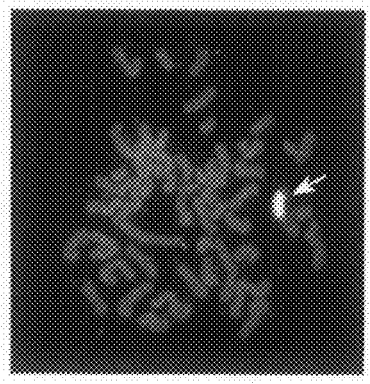
Figure 10:
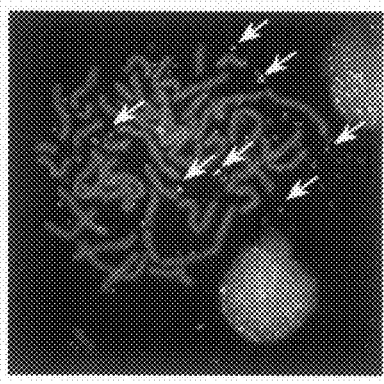

FIG. 10 illustrates the result of the detection of the base sequence derived from the pSFVdhfr/d2EGFP plasmid, by FISH method. FIG. 10(a) shows the result of clone 4. FIG. 10(b) shows the result of clone 5. FIG. 10(c) shows the result of clone 6. FIG. 10(d) shows the result of clone 9. The arrows in FIG. 10 are pointing the base sequence derived from the pSFVdhfr/d2EGFP plasmid.

The results shown in FIG. 10 showed that the base sequence derived from the pSFVdhfr/d2EGFP plasmid was amplified on HSR in clones 4, 5, and 6, but the base sequence was amplified on DM in clone 9.

For 4 clones, induction with Doxycycline (Clontech Laboratories Inc.; 1 µg/ml) was carried out and 5-aza (0 µM, 1 µM or 3 µM) was added in the medium. After 1 week culturing, the level of expression of d2EGFP in each clone was analyzed by using a cell sorter.

Figure 11:
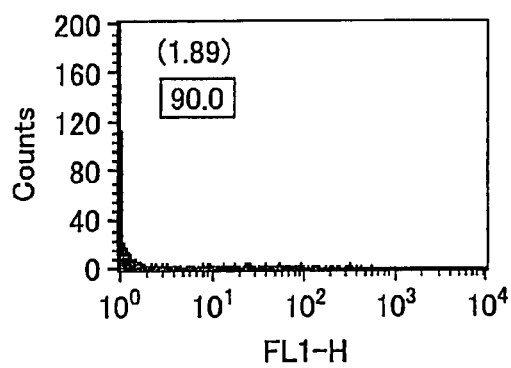
FIG. 11(a) is a view illustrating the result of analysis on the level of the expression of d2EGFP in clone 4 after the expression of d2EGFP was induced with Doxycycline and one-week incubation without adding 5-aza in a medium where clone 4 was obtained in Example 7 and the analysis was carried out by using a cell sorter.
FIG. 11(b) is a view illustrating the result of analysis on the level of the expression of d2EGFP in clone 4 after the expression of d2EGFP was induced with Doxycycline and one-week incubation with 5-aza (final concentration of 1 μM) added in a medium where clone 4 was obtained in Example 7 and the analysis was carried out by using a cell sorter.
FIG. 11(c) is a view illustrating the result of analysis on the level of the expression of d2EGFP in clone 4 after the expression of d2EGFP was induced with Doxycycline and one-week incubation with 5-aza (final concentration of 3 μM) added in a medium where clone 4 was obtained in Example 7 and the analysis was carried out by using a cell sorter.
Figure 11:
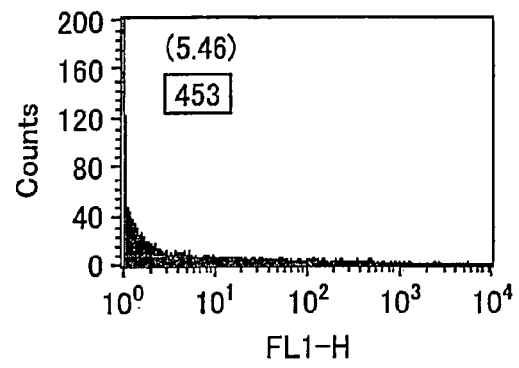
Figure 11:
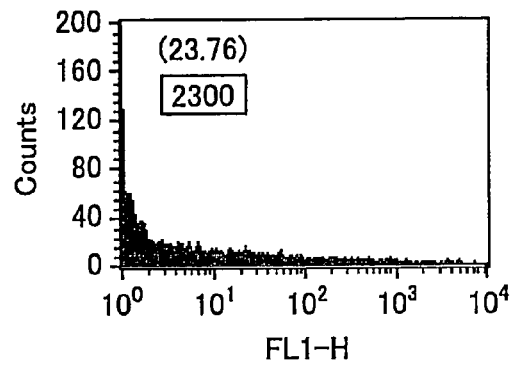

The results are illustrated in FIGS. 11, 12, 13, and 14. FIG. 11 illustrates the result of clone 4. FIG. 11(a) illustrates a result of a case where 5-aza was not added (0 µM). FIG. 11(b) illustrates a result of a case where 1 µM of 5-aza was added (1 µM). FIG. 11(c) illustrates a result of a case where 3 µM of 5-aza was added (3 µM).

Figure 12:
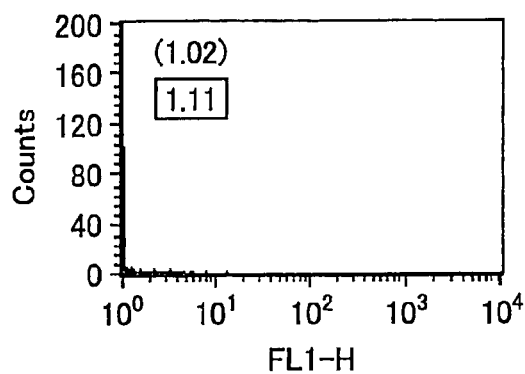
FIG. 12(a) is a view illustrating the result of analysis on the level of the expression of d2EGFP in clone 5 after the expression of d2EGFP was induced with Doxycycline and one-week incubation without adding 5-aza in a medium where clone 5 was obtained in Example 7 and the analysis was carried out by using a cell sorter.
FIG. 12(b) is a view illustrating the result of analysis on the level of the expression of d2EGFP in clone 5 after the expression of d2EGFP was induced with Doxycycline and one-week incubation with 5-aza (final concentration of 1 μM) added in a medium where clone 5 was obtained in Example 7 and the analysis was carried out by using a cell sorter.
FIG. 12(c) is a view illustrating the result of analysis on the level of the expression of d2EGFP in clone 5 after the expression of d2EGFP was induced with Doxycycline and one-week incubation with 5-aza (final concentration of 3 μM) added in a medium where clone 5 was obtained in Example 7 and the analysis was carried out by using a cell sorter.
Figure 12:
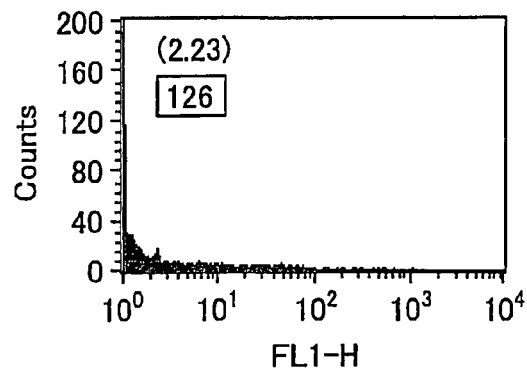
Figure 12:
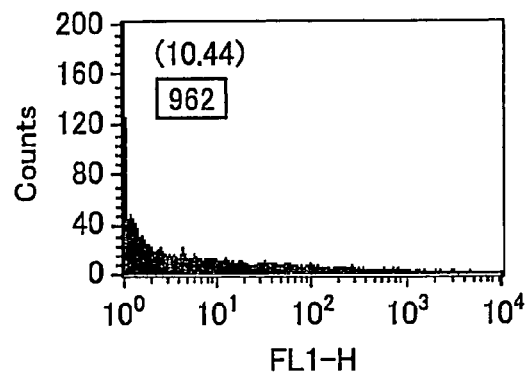

FIG. 12 illustrates the result of clone 5. FIG. 12(a) illustrates a result of a case where 5-aza was not added (0 µM). FIG. 12(b) illustrates a result of a case where 1 µM of 5-aza was added (1 µM). FIG. 12(c) illustrates a result of a case where 3 µM of 5-aza was added (3 µM).

Figure 13:
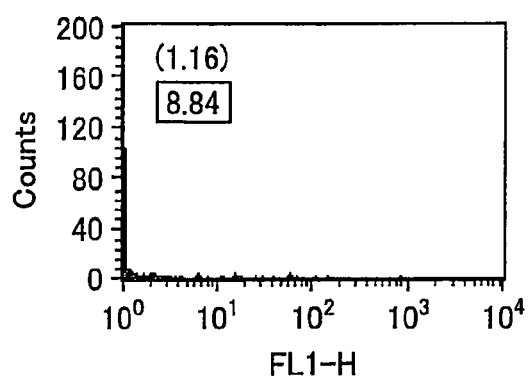
FIG. 13(a) is a view illustrating the result of analysis on the level of the expression of d2EGFP in clone 6 after the expression of d2EGFP was induced with Doxycycline and one-week incubation without adding 5-aza in a medium where clone 6 was obtained in Example 7 and the analysis was carried out by using a cell sorter.
FIG. 13(b) is a view illustrating the result of analysis on the level of the expression of d2EGFP in clone 6 after the expression of d2EGFP was induced with Doxycycline and one-week incubation with 5-aza (final concentration of 1 μM) added in a medium where clone 6 was obtained in Example 7 and the analysis was carried out by using a cell sorter.
FIG. 13(c) is a view illustrating the result of analysis on the level of the expression of d2EGFP in clone 6 after the expression of d2EGFP was induced with Doxycycline and one-week incubation with 5-aza (final concentration of 3 μM) added in a medium where clone 6 was obtained in Example 7 and the analysis was carried out by using a cell sorter.
Figure 13:
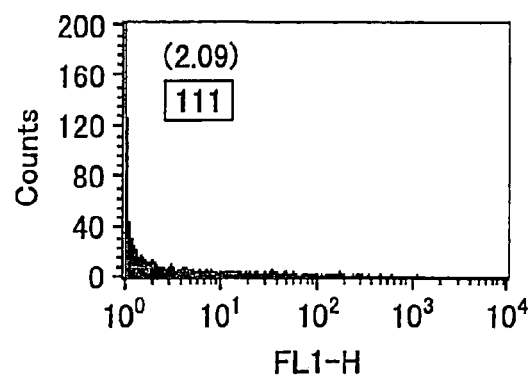
Figure 13:
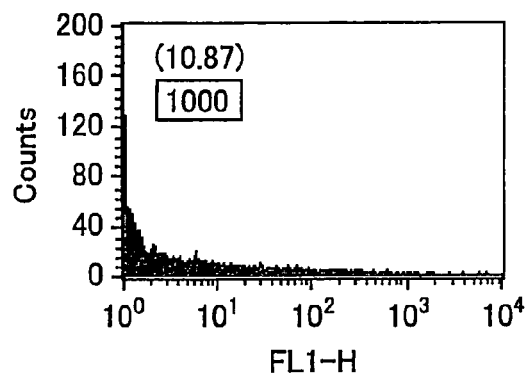

FIG. 13 illustrates the result of clone 6. FIG. 13(a) illustrates a result of a case where 5-aza was not added (0 µM). FIG. 13(b) illustrates a result of a case where 1 µM of 5-aza was added (1 µM). FIG. 13(c) illustrates a result of a case where 3 µM of 5-aza was added (3 µM).

Figure 14:
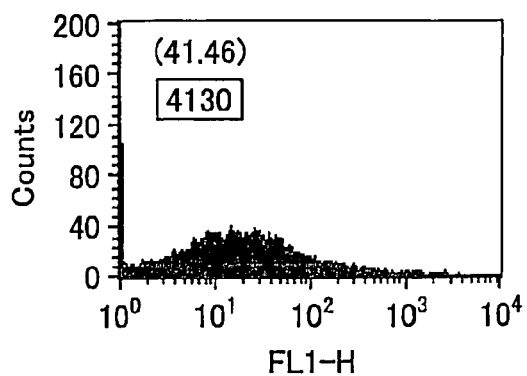
FIG. 14(a) is a view illustrating the result of analysis on the level of the expression of d2EGFP in clone 9 after the expression of d2EGFP was induced with Doxycycline and one-week incubation without adding 5-aza in a medium where clone 9 was obtained in Example 7 and the analysis was carried out by using a cell sorter.
FIG. 14(b) is a view illustrating the result of analysis on the level of the expression of d2EGFP in clone 9 after the expression of d2EGFP was induced with Doxycycline and one-week incubation with 5-aza (final concentration of 1 μM)
Figure 14:
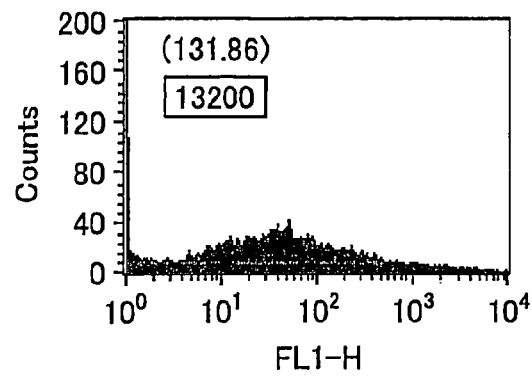
Figure 14:
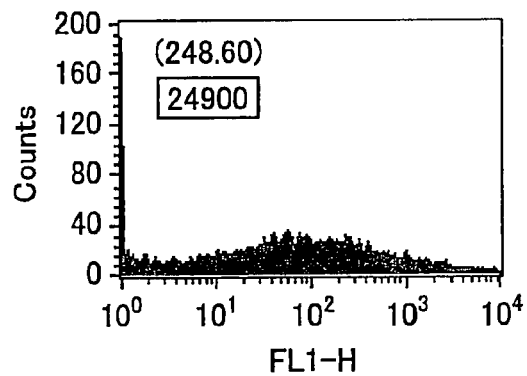

FIG. 14 illustrates the result of clone 9. FIG. 14(a) illustrates a result of a case where 5-aza was not added (0 µM). FIG. 14(b) illustrates a result of a case where 1 µM of 5-aza was added (1 µM). FIG. 14(c) illustrates a result of a case where 3 µM of 5-aza was added (3 µM).

In FIGS. 11 to 13, the value in parenthesis is an average of fluorescence intensities (i.e., average fluorescence intensity), and boxed value is an accumulated fluorescence intensity.

FIG. 11 illustrate clone 4 as follows: an average fluorescence intensity and an accumulate fluorescence intensity indicating a level of expression in the case of no addition of 5-aza in the medium (0 µM) were 1.89 and 90.0 respectively; an average fluorescence intensity and an accumulate fluorescence intensity in the case of the addition of 1 µM of 5-aza in the medium were 5.46 and 453 respectively; and an average fluorescence intensity and an accumulate fluorescence intensity in the case of the addition of 3 μM of 5-aza in the medium were 23.76 and 2300 respectively.

FIG. 12 illustrate clone 5 as follows: an average fluorescence intensity and an accumulate fluorescence intensity indicating a level of expression in the case of no addition of 5-aza in the medium (0 μM) were 1.02 and 1.11 respectively; an average fluorescence intensity and an accumulate fluorescence intensity in the case of the addition of 1 μM of 5-aza in the medium were 2.23 and 126 respectively; and an average fluorescence intensity and an accumulate fluorescence intensity in the case of the addition of 3 μM of 5-aza in the medium were 10.44 and 962 respectively.

FIG. 13 illustrate clone 6 as follows: an average fluorescence intensity and an accumulate fluorescence intensity indicating a level of expression in the case of no addition of 5-aza in the medium (0 μM) were 1.16 and 8.84 respectively; an average fluorescence intensity and an accumulate fluorescence intensity in the case of the addition of 1 μM of 5-aza in the medium were 2.09 and 111 respectively; and an average fluorescence intensity and an accumulate fluorescence intensity in the case of the addition of 3 μM of 5-aza in the medium were 10.87 and 1000 respectively.

FIG. 14 illustrate clone 9 as follows: an average fluorescence intensity and an accumulate fluorescence intensity indicating a level of expression in the case of no addition of 5-aza in the medium (0 μM) were 41.46 and 4130 respectively; an average fluorescence intensity and an accumulate fluorescence intensity in the case of the addition of 1 μM of 5-aza in the medium were 131.86 and 13200 respectively; and an average fluorescence intensity and an accumulate fluorescence intensity in the case of the addition of 3 μM of 5-aza in the medium were 248.60 and 24900 respectively.

From the results illustrated in FIGS. 11 to 14, it was demonstrated that the level of the expression of d2EGFP was very low in clones (clone 4, clone 5, and clone 6) in which the base sequence derived from the pSFVdhfr/d2EGFP plasmid was amplified on HSR, but that this level of the expression of d2EGFP could be increased by adding 5-aza to the medium. On the other hand, it was found that the addition of 5-aza in the medium was not necessary to attain a high level of the expression of d2EGFP (average fluorescence intensity: 41.46, accumulate fluorescence intensity: 4130) in the clone (clone 9) in which the base sequence derived from the pSFVdhfr/d2EGFP plasmid was amplified on DM, but that the addition of 5-aza in the medium dramatically increased the level of expression in such a clone (average fluorescence intensity: 131.86 or 248.60, accumulate fluorescence intensity: 13200 or 24900).

Therefore, it was shown that a high level of expression of a target protein can be attained by selecting a clone in which gene amplification occurs on DM.

Example 8

Effect of Cotransfection to attaining High Expression of Transcription Activating Factor for Activation Promoter for Controlling Expression of Target Protein (Method and Result)

An equimolar mixture of a plasmid (pSFVdhfr/d2EGFP) and pTet-ON plasmid (Clontech Laboratories Inc.) was simultaneously transfected into human colon cancer COLO 320DM cells. The plasmid (pSFVdhfr/d2EGFP) was a plasmid having (a) IR and MAR derived from human DHFR gene locus, (b) Blasticidin tolerance gene, and (c) d2EGFP gene that was under control of TRE-promoter (Tetracycline inducing promoter). Meanwhile, the pTet-ON plasmid was a plasmid having Tet-ON gene encoding the transcription activating factor (Tet-ON protein) of TRE-promoter. The cells were selected with 5 μg/ml of Blasticidin thereby obtaining a polyclonal population of transformed cells. TRE-promoter was activated by adding 1 μg/ml of Doxycycline (Clontech Laboratories Inc.) in the medium of a cell culturing solution of the polyclonal population, thereby inducing the expression of d2EGFP.

FIG. 15(a) illustrates a phase contrast microscopic image (×200) of the polyclonal population before the addition of Doxycycline, while FIG. 15(b) illustrates a fluorescence microscopic image (×200) thereof. FIG. 15(c) illustrates a phase contrast microscopic image (×200) of the polyclonal population after the addition of Doxycycline, while FIG. 15(d) illustrates a fluorescence microscopic image (×200) thereof.

According to FIGS. 15(a) to (d), fluorescence intensity of d2EGFP was very weak before the addition of Doxycycline, but the fluorescence intensity of d2EGFP was increased by the addition of Doxycycline. Thus, it was confirmed that the addition of Doxycycline (Clontech Laboratories Inc.) in the medium activated TRE-promoter and thereby inducing the expression of d2EGFP in the polyclonal population of the transformed cells in which pSFVdhfr/d2EGFP and the pTet-ON plasmid were simultaneously transfected.

Figure 16:
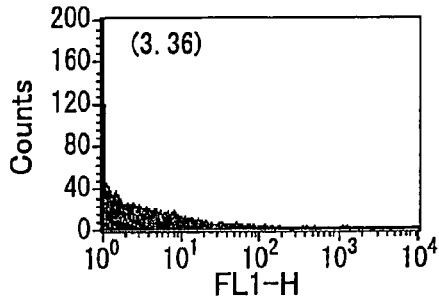
Figure 16:
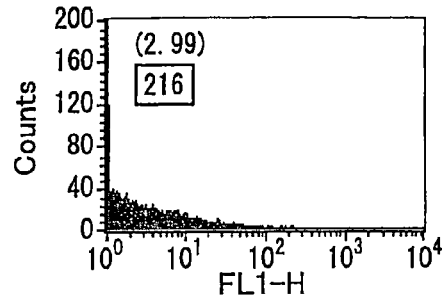
Figure 16:
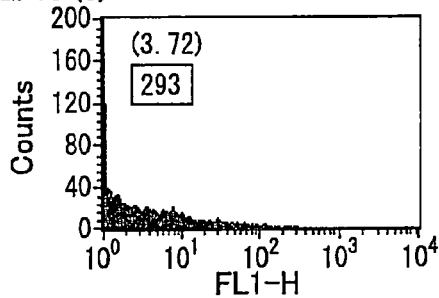
Figure 16:
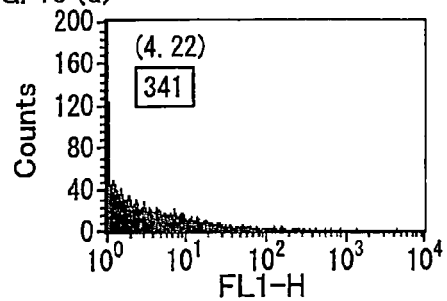
Figure 16:
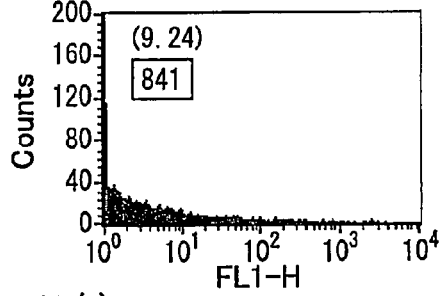
Figure 16:
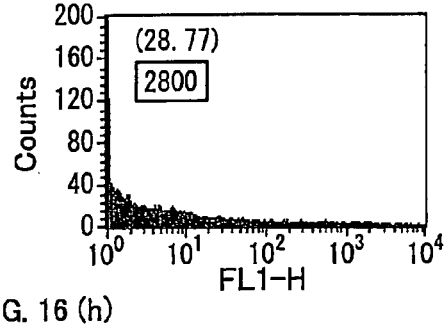
Figure 16:
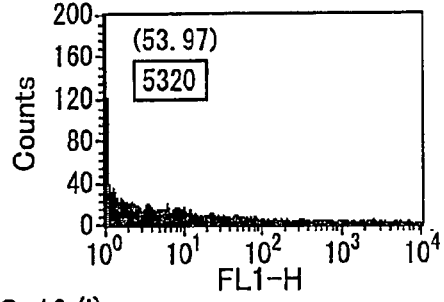
Figure 16:
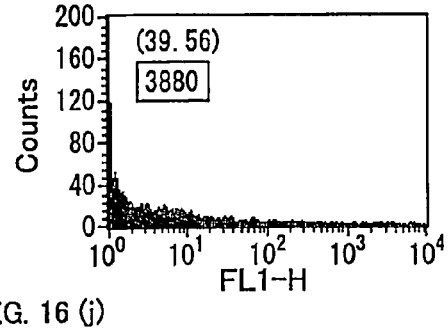
Figure 16:
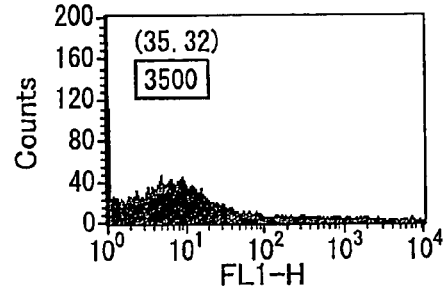
Figure 16:
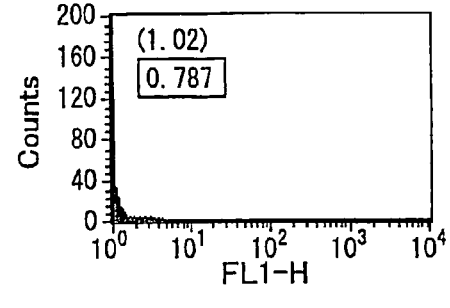

Next, after the expression of d2EGFP was induced by Doxycycline, the level of the expression of d2EGFP was analyzed by using a cell sorter so as to find a change in the level of the expression of d2EGFP over time. The results are shown in FIG. 16. FIG. 16(a) shows the reading before the addition of Doxycycline. FIG. 16(b) shows the reading 1 hour after the addition of Doxycycline. FIG. 16(c) shows the reading 3 hours after the addition of Doxycycline. FIG. 16(d) shows the reading 6 hours after the addition of Doxycycline. FIG. 16(e) shows the reading 15 hours after the addition of Doxycycline. FIG. 16(f) shows the reading 24 hours (1 day) after the addition of Doxycycline. FIG. 16(g) shows the reading 48 hours (2 days) after the addition of Doxycycline. FIG. 16(h) shows the reading 120 hours (5 days) after the addition of Doxycycline. FIG. 16(i) shows the reading approximately two weeks from the addition of Doxycycline. In FIG. 16, the value in parenthesis is an average of fluorescence intensities (i.e., average fluorescence intensity), and boxed value is an accumulated fluorescence intensity.

FIG. 17 illustrates a graph plotting the averages (i.e., average fluorescence intensities: indicated by filled circles in FIG. 17) and living cell ratio (a ratio of living cells over total cell number: indicated by open circles) of the level of the expression of d2EGFP against time. According to FIG. 17, the polyclonal population thus obtained showed very low level of the expression of d2EGFP before the addition of Doxycycline, the level of the expression was peaked in 1 to 2 days after the addition of Doxycycline. The level was maintained high even after two weeks lapsed (labeled as "2wk" in FIG. 17). Moreover, in the polyclonal population, no decrease in the survival ratio of the cells due to the expression of d2EGFP induced by Doxycycline and the cells were proliferated normally expressing d2EGFP at a high level.

The result of analysis on expression of d2EGFP of a negative control by using a cell sorter is shown in FIG. 16(j). The negative control was prepared as follows. Into the pSFV-V plasmid having no origin of replication and no nuclear matrix attachment region, the d2EGFP gene under control of the TRE-promoter was embedded thereby constructing a plasmid. The plasmid thus constructed was transfected in Tet-ON cells thereby obtaining a polyclonal population of transformed cells. In the polyclonal population, the expression of d2EGFP was induced by Doxycycline. According to FIG. 16(j), the negative control had a level of expression of d2EGFP which had an average fluorescence intensity of 1.02 and accumulated fluorescence intensity of 0.787.

Meanwhile, an average fluorescence intensity was 2.99 and accumulated fluorescence intensity was 216 one hour after the addition of Doxycycline (FIG. 16(b)). An average fluorescence intensity was 3.72 and accumulated fluorescence intensity was 293 three hours after the addition of Doxycycline (FIG. 16(c)). An average fluorescence intensity was 4.22 and accumulated fluorescence intensity was 341 six hours after the addition of Doxycycline (FIG. 16(d)). An average fluorescence intensity was 9.24 and accumulated fluorescence intensity was 841 fifteen hours after the addition of Doxycycline (FIG. 16(e)). An average fluorescence intensity was 28.77 and accumulated fluorescence intensity was 2800 twenty four hours after the addition of Doxycycline (FIG. 16(f)). An average fluorescence intensity was 53.97 and accumulated fluorescence intensity was 5320 forty eight hours (2 days) after the addition of Doxycycline (FIG. 16(g)). An average fluorescence intensity was 39.56 and accumulated fluorescence intensity was 3880 one hundred twenty hours (5 days) after the addition of Doxycycline (FIG. 16(h)). An average fluorescence intensity was 35.32 and accumulated fluorescence intensity was 3500 two weeks after the addition of Doxycycline (FIG. 16(i)).

From these results, it was found that the polyclonal populations obtained by the method according to the present Example showed a very high level of expression after the induction of the expression, and the level was approximately 300 times to 7000 times greater than the negative control in terms of the accumulated fluorescence intensity.

Figure 18:
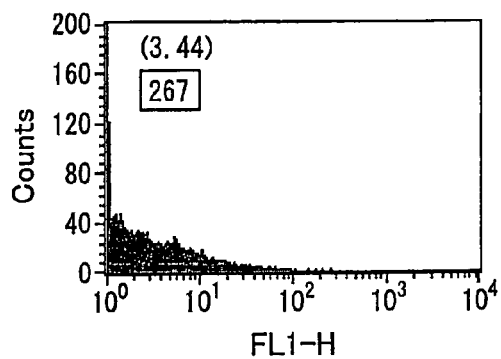
Figure 18:
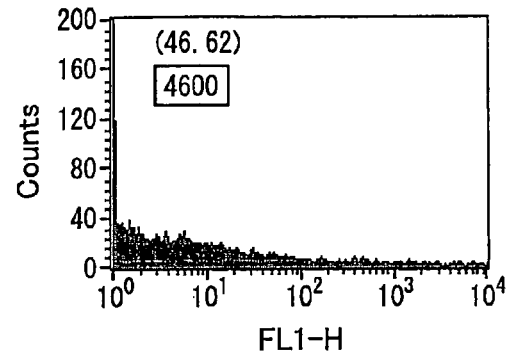
Figure 18:
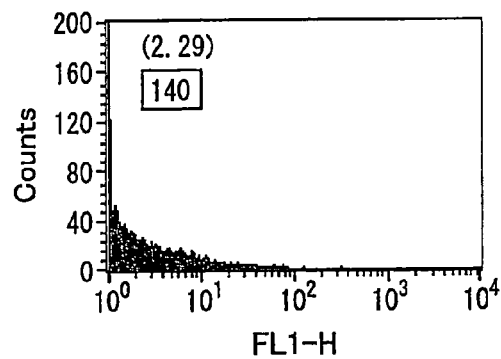
Figure 18:
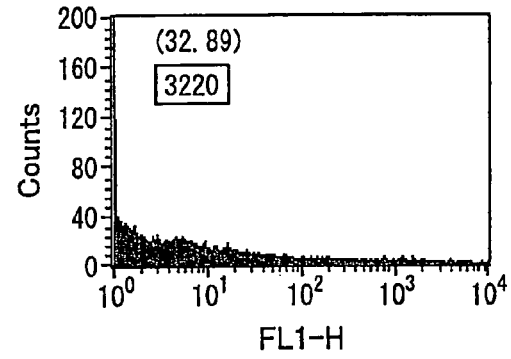
Figure 18:
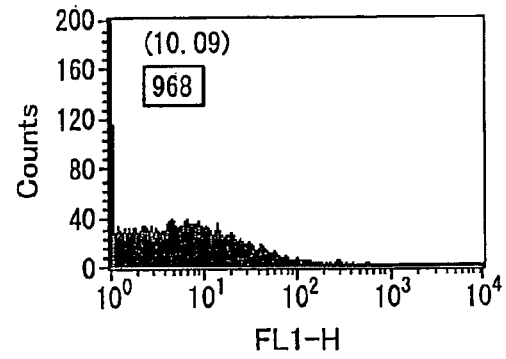
Figure 18:
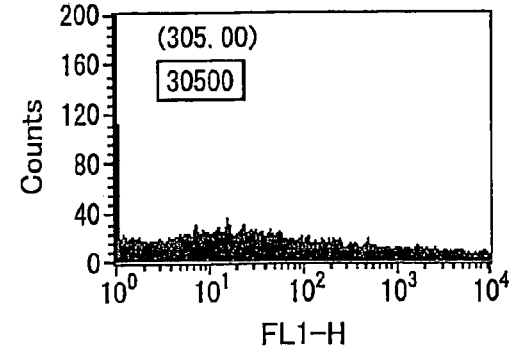

Furthermore, given 5 clones selected from among the polyclonal population thus obtained by the method according to the present Example were analyzed by a cell sorter so as to find the level of the expression of d2EGFP after the expression was induced. Typical examples of the results (three clones) are shown in FIG. 18. FIGS. 18(a) and 18(b) show the results of clone A, where FIG. 18(a) shows the result before the induction of the expression and FIG. 18(b) shows the result after the induction of the expression. FIGS. 18(c) and 18(d) show the results of clone B, where FIG. 18(c) shows the result before the induction of the expression and FIG. 18(d) shows the result after the induction of the expression. FIGS. 18(e) and 18(f) show the results of clone C, where FIG. 18(e) shows the result before the induction of the expression and FIG. 18(f) shows the result after the induction of the expression. In FIG. 18, the value in parenthesis is an average of fluorescence intensities (i.e., average fluorescence intensity), and boxed value is an accumulated fluorescence intensity.

From FIG. 18, it was understood that it was possible to easily attain a clone having a very high level of expression of the target protein (d2EGFP) from the polyclonal population obtained by the method according to the present Example.

Furthermore, the method according to the present Example is expected to attain a high expression of the target protein (d2EGFP) from the amplified gene on HSR. This can be confirmed by the following experiment: A mixture of pSFVdhfr and pECMS2Beta was cotransfected to human colon cancer COLO 320DM cells by lipofection, where pSFVdhfr was a plasmid having an origin of replication and a nuclear matrix attachment region, and pECMS2Beta was a plasmid having, in the downstream of LacO (lactose operator)-repeat sequence and TRE-promoter, an MS2 junction sequence (pECMS2Beta was kindly provided from Dr. Susan Janicki and Dr. David Spector (cold Spring Harbor Laboratory); see "Janicki, S. M., T. Tsukamoto, S. E. Salghetti, W. P. Tansey, R. Sachidanandam, K. V. Prasanth, T. Ried, Y. Shav-Tal, E. Bertrand, R. H. Singer, and D. L. Spector. 2004. From silencing to gene expression: real-time analysis in single cells. Cell. 116:683-698.").

The human colon cancer COLO 320DM cells used here were cloned cells which became Neomycin tolerance by transfecting the pLacR-CFP plasmid by lipofection in advance, where the pLacR-CFP plasmid was a plasmid that expressed a fused protein of LacR (lactose repressor) and CFP (cyan fluorescence protein), and was kindly provided from Dr. Susan Janicki and Dr. David Spector (cold Spring Harbor Laboratory); see "Janicki, S. M., T. Tsukamoto, S. E. Salghetti, W. P. Tansey, R. Sachidanandam, K. V. Prasanth, T. Ried, Y. Shav-Tal, E. Bertrand, R. H. Singer, and D. L. Spector. 2004. From silencing to gene expression: real-time analysis in single cells. Cell. 116:683-698."

As a result, a clone in which HSR was formed by coamplification of both the plasmids. In the clone, HSR showed cyan fluorescence because LacR-CFP is bound with the LacO sequence in HSR.

Moreover, the pTet-ON plasmid (Clontech Laboratories Inc.) and a plasmid for expressing a fused protein of MS2 and YFP (yellow fluorescence protein) (which was kindly provided from Dr. Susan Janicki and Dr. David Spector (cold Spring Harbor Laboratory); see "Janicki, S. M., T. Tsukamoto, S. E. Salghetti, W. P. Tansey, R. Sachidanandam, K. V. Prasanth, T. Ried, Y. Shav-Tal, E. Bertrand, R. H. Singer, and D. L. Spector. 2004. From silencing to gene expression: real-time analysis in single cells. Cell. 116:683-698.") were simultaneously transfected in the clone by the electroporation After 2.5 hours, 1 µg/ml of Doxycycline (Clontech Laboratories Inc.) was added to the medium. At this stage, the expressed Tet-ON protein and Doxycycline activated the TRE-promoter in HSR, thereby causing transcription of RNA for encoding the fused protein of MS2 and YFP (yellow fluorescence protein). This RNA has a MS2 junctional sequence. Because of this, the fused protein of MS2 and YFP is bound thereto thereby showing yellow fluorescence.

A typical photographs showing the result are shown in FIG. 19. In FIG. 19, A, B and C are fluorescence microscopic images (labeled as "–Dox" on the left) of the clones before the induction of the expression by Doxycycline, while D and E are fluorescence microscopic images (labeled as "+Dox 1.5 hr" on the left) of the clones 1.5 hours after the induction of the expression by Doxycycline. Moreover, the images labeled as "Lamin B" on the top are images in which nuclear lamina are visualized by indirect fluorescent antibody technique using anti-Lamin B antibody (Santa Cruz Biotechnologies Inc.). The images labeled as "CFP-HSR" on the top are images in which HSR is visualized using cyan fluorescence protein. The images labeled as "YFP-MS2 RNA" on the top are images in which RNA is visualized using YFP (yellow fluorescence protein). The images labeled as "Merge" on the top are images in which the three images are overlapped.

Before the induction of the expression with Doxycycline, HSR (indicated by the arrows in FIG. 19) visualized with cyan color of CFP (cyan fluorescence protein) was heterochromatized and thus having small and shrunk spherical structures. It was clearly observed that the induction of the expression with Doxycycline caused HSR in cyan color to be loosened up largely and RNA (indicated by being circled) visualized in yellow fluorescence was coming out therefrom.

These results showed that the activation of the TRE-promoter with the Tet-ON protein and Doxycycline loosens heterochromatized HSR formed by the plasmid having IR and MAR, thereby activating the RNA transcription.

Example 9

Effect of Cotransfection for High Expression of Transcription Activation Factor of Promoter for Controlling Expression of Target Protein, and Treating Cells with 5-aza-2'-deoxycytidine (Method and Result)

Figure 20:
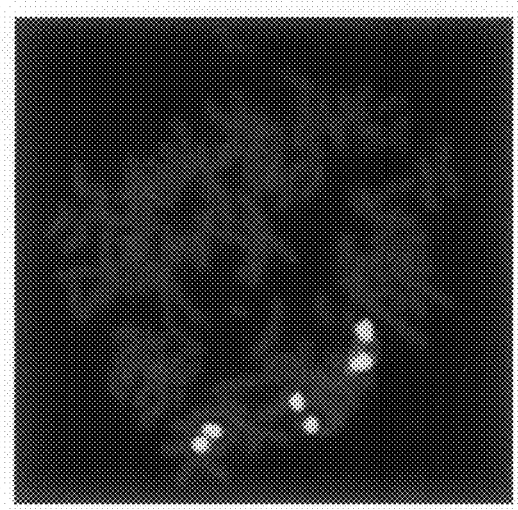
Figure 20:
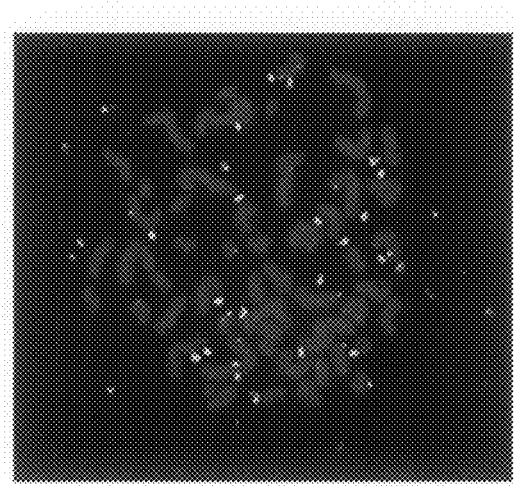

An equimolar mixture of a plasmid (pSFVdhfr/d2EGFP) and pTet-ON plasmid (Clontech Laboratories Inc.) was simultaneously transfected into human colon cancer COLO 320DM cells. The plasmid (pSFVdhfr/d2EGFP) was a plasmid having (a) IR and MAR derived from human DHFR gene locus, (b) Blasticidin tolerance gene, and (c) d2EGFP gene that was under control of TRE-promoter (Tetracycline inducing promoter). Meanwhile, the pTet-ON plasmid was a plasmid having Tet-ON gene encoding the transcription activating factor (Tet-ON protein) of TRE-promoter. The cells were selected with 5 μg/ml of Blasticidin thereby obtaining a polyclonal population of transformed cells. From the polyclonal population, given 10 clones were selected by limiting dilution. Then, from among the 10 clones a clone in which a base sequence derived from the pSFVdhfr/d2EGFP plasmid was amplified on HSR (this clone is referred to as "HSR clone" hereinafter for easy explanation), and a clone in which the base sequence is amplified on DM (this clone is referred to as "DM clone" hereinafter for easy explanation) were screened. FIGS. 20(a) and 20(b) respectively illustrate the results of detection of the base sequence derived from the transfected pSFVdhfr/d2EGFP plasmid for HSR clone and DM clone. In FIG. 20, the detected base sequence derived from the pSFVdhfr/d2EGFP plasmid is indicated by the arrow. The limiting dilution and the screening was carried out as described in Example 7.

Figure 21:
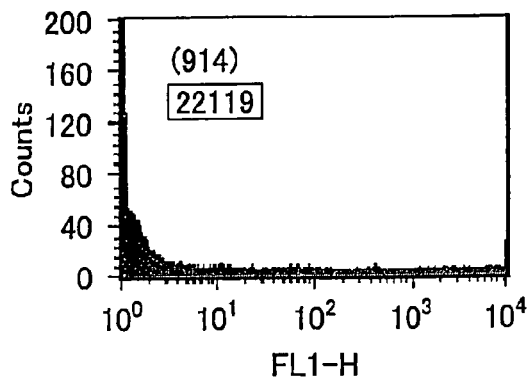
Figure 21:
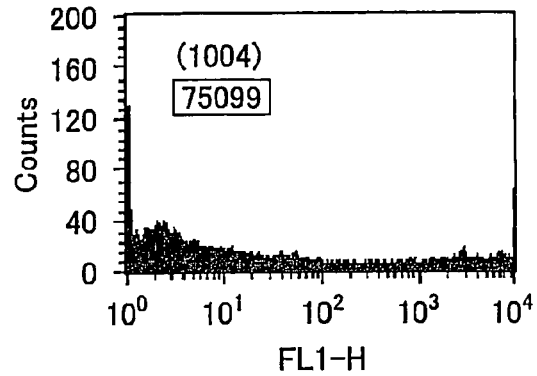
Figure 21:
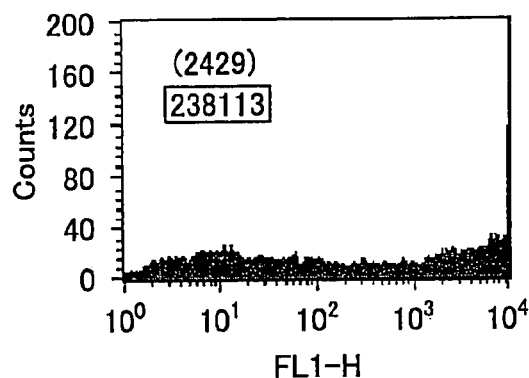
Figure 21:
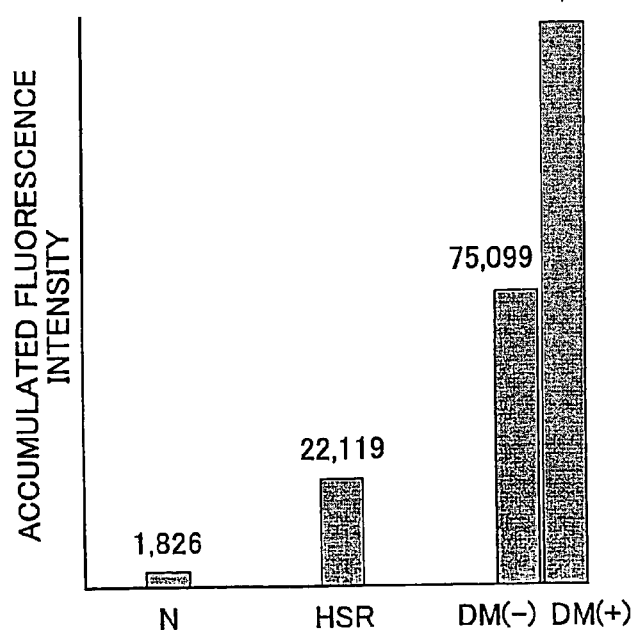

In each culture solution of the two clones, 3 μM of 5-aza was added and thereby the clones were treated with 5-aza for 3 days. Then, Doxycycline (Clontech Laboratories Inc.; 1 μg/ml) was added in the couture solutions and thereby the expression of d2EGFP was induced for 2 days. After the culturing, the level of the expression of d2EGFP in each clone was analyzed by a cell sorter. Moreover, as a negative control a polyclonal population of transformed cells was prepared in the same way except that pSFV-V plasmid having no origin of replication and no nuclear matrix attachment region was used in replacement of pSFVdhfr/d2EGFP. This polyclonal population of transformed cells was subjected to the induction of expression of d2EGFP with Doxycycline and a level of the expression of d2EGFP therein was analyzed by using the cell sorter in the same way as described above. The results are illustrated in FIGS. 21(a) to 21(c). FIG. 21(a) illustrates the result of the fluorescence intensity measurements of HSR clone two days after the addition of Doxycycline. FIG. 21(b) illustrates the result of the fluorescence intensity measurements of DM clone (not treated with 5-aza) two days after the addition of Doxycycline. FIG. 21(c) illustrates the result of the fluorescence intensity measurements of DM clone (treated with 5-aza) two days after the addition of Doxycycline. FIG. 21, the value in parenthesis is an average of fluorescence intensities (i.e., average fluorescence intensity), and boxed value is an accumulated fluorescence intensity. Moreover, FIG. 21(d) is a bar graph showing the accumulated fluorescence intensities two days after the addition of Doxycycline for the negative control, HSR clone, and DM clones (treated and not treated with 5-aza).

According to FIG. 21(d), the accumulated fluorescence intensity of the negative control (labeled as "N" in FIG. 21(d)) was 1826, the accumulated fluorescence intensity of the HSR clone (labeled as "HSR" in FIG. 21(d)) was 22119, the accumulated fluorescence intensity of the DM clone (not treated with 5-aza; labeled as "DM(−)" in FIG. 21(d)) was 75099, and the accumulated fluorescence intensity of DM clone (treated with 5-aza; labeled as "DM(+)" in FIG. 21(d)) was 238113. This showed that the HSR clone and DM clones had significantly higher levels of the expression of d2EGFP than the negative control clone, and that the 5-aza treatment improved the level of the expression of d2EGFP.

Example 10

Effect of the Present Invention in CHO Cells (Method and Result)

The present embodiment was carried out in the same way as described in Example 9, except that the cells to which the plasmids were transfected were CHO-K1 cells (kindly provided from Cell Research Center for Biomedical Research, Institute of Development, Aging and Cancer, Tohoku University).

Figure 22:
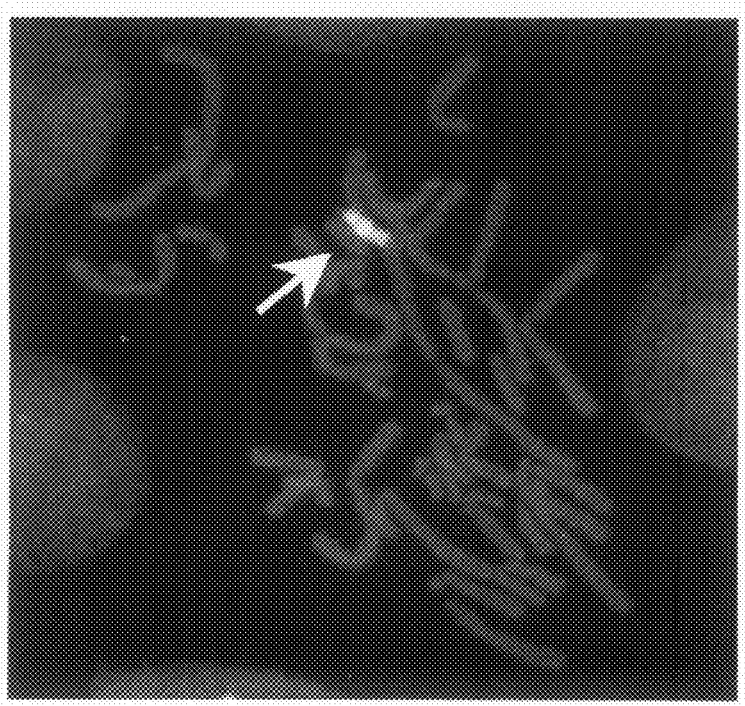
Figure 22:
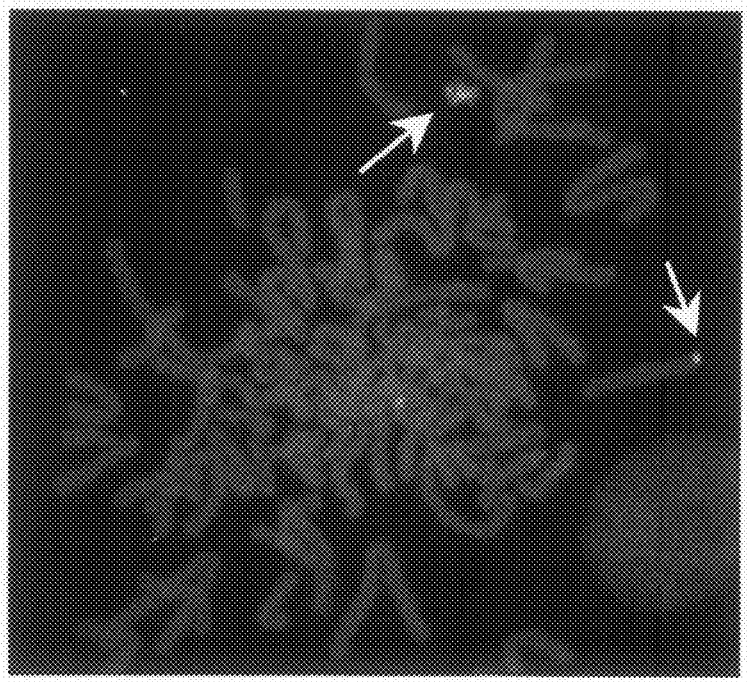

As a result, a clone in which a base sequence derived from the pSFVdhfr/d2EGFP plasmid was amplified on HSR (this clone is referred to as "HSR clone" hereinafter for easy explanation), and a clone in which the base sequence is amplified on DM (this clone is referred to as "DM clone" hereinafter for easy explanation) were successfully isolated from the CHO cells. This proved that the present invention is applicable to cells other than tumor cells such as COLO 320 DM cells. FIG. 22(a) illustrates the result of the detection of the base sequence of the transfected pSFVdhfr/d2EGFP plasmid in the isolated HSR clone of the CHO cells by the FISH method. FIG. 22(b) illustrates the result of the detection of the DM clone of the CHO cells. The detected base sequence of the transfected pSFVdhfr/d2EGFP plasmid is indicated by the arrow in FIG. 22.

FIG. 23(a) illustrates the result of fluorescence intensity measurement of that clone two days after the addition of Doxycycline, which had the highest level of the expression of d2EGFP according to the cell sorter (this clone is referred to as "max clone" hereinafter for easy explanation). Moreover, FIG. 23(b) illustrates accumulated fluorescence intensities (2 days after the addition of Doxycycline) of a polyclonal population of transformed cells in a negative control, a polyclonal population of transformed cells in the present embodiment, and the max clone.

According to FIG. 23(b), the polyclonal population (labeled as "P" in FIG. 23(b)) of the transformed cells in the present embodiment had the accumulated fluorescence intensity of 14022, and the max clone (labeled as "M" in FIG. 23(b)) of the transformed cells in the present embodiment had the accumulated fluorescence intensity of 167865, while the polyclonal population (labeled as "NP" in FIG. 23(b)) of the transformed cells in the negative control had the accumulated fluorescence intensity of 296. This demonstrated that the polyclonal population of the transformed cells in the present embodiment and the max clone had significantly higher levels of the expression of d2EGFP than the polyclonal population of the transformed cells in the negative control. Especially, the max clone isolated from the polyclonal population had further higher levels of the expression of d2EGFP than the negative control.

FIG. 23(c) illustrates the result of detection of the base sequence of the transfected pSFVdhfr/d2EGFP plasmid in the max clone by the FISH method. The detected base sequence of the pSFVdhfr/d2EGFP plasmid is indicated by the arrow in FIG. 23(c). From FIG. 23(c), it can be understood that the max clone is a clone in which the base sequence derived the pSFVdhfr/d2EGFP plasmid was amplified on HSR (relatively short HSR).

INDUSTRIAL APPLICABILITY

As described above, a method and means for releasing transcription repression caused by a repeated gene sequence are provided by a method and a kit according to the present invention. As a result, mass production of useful protein by gene amplification can be done by the method and the kit according to the present invention. Therefore, the present invention is applicable to protein-producing industries such as pharmaceutical, chemical, food, cosmetic, textile industries, etc.

The invention claimed is:

1. A method of expressing a protein from a repeated sequence formed in CHO cells in which gene amplification is induced, the protein having been under expression repression, the method comprising
(1) transfecting into the CHO cells
 (a) a gene structure comprising
  (i) a first polynucleotide having an origin of replication and a nuclear matrix attachment region that functions in eukaryotic cells and a selection marker that is a drug resistance gene which confers resistance to an antibiotic, and
  (ii) a second polynucleotide having a promoter region controllably linked to a polynucleotide encoding a protein to be expressed and an insulator sequence; and
 (b) a polynucleotide encoding a transcription activation factor of the promoter; and
(2) subsequently treating the transfected CHO cells with 5-aza-2'-deoxycytidine at a concentration in the range of 1-2 µM and culturing the transfected CHO cells sequentially in a medium of increasing concentrations of the antibiotic whereby the concentration of the antibiotic increases by 10% to 30% per 24 hours.

2. The method as set forth in claim 1, further comprising selecting CHO cells in which the gene amplification occurs on a double minute chromosome.

3. The method as set forth in claim 1, wherein the origin of replication is an origin of replication of a c-myc locus, a dihydrofolate reductase locus, or a β-globin locus.

4. The method as set forth in claim 1, wherein the nuclear matrix attachment region is a nuclear matrix attachment region of an IgK locus, a SV40 initiation region, or a dihydrofolate reductase locus.

5. The method as set forth in claim 1, wherein the transfection is simultaneous.

6. A transformed CHO cell selected by
(1) transfecting into the CHO cell,
 (a) a gene structure comprising
  a first polynucleotide having an origin of replication and a nuclear matrix attachment region that functions in eukaryotic cells and a selection marker that is a drug resistance gene which confers resistance to an antibiotic, and
  (ii) a second polynucleotide having a promoter region controllably linked to a polynucleotide encoding a protein to be expressed and an insulator sequence; and
 (b) a polynucleotide encoding a transcription activation factor of the promoter; and
(2) subsequently treating the transfected CHO cell with 5-aza-2'-deoxycytidine at a concentration in the range of 1-2 µM and culturing the transfected CHO cell sequentially in a medium of increasing concentrations of the antibiotic whereby the concentration of the antibiotic increases by 10% to 30% per 24 hours.

7. The transformant as set forth in claim 6, wherein the origin of replication is an origin of replication of a c-myc locus, a dihydrofolate reductase locus, or a β-globin locus.

8. The transformant as set forth in claim 6, wherein the nuclear matrix attachment region is a nuclear matrix attachment region of an IgK locus, a SV40 initiation region, or a dihydrofolate reductase locus.

9. The transformant as set forth in claim 6, wherein the transfection is simultaneous.

* * * * *